(12) United States Patent
Xie et al.

(10) Patent No.: US 10,898,576 B2
(45) Date of Patent: Jan. 26, 2021

(54) GLUCOCORTICOID COMBINED WITH POLYETHYLENE GLYCOL-MODIFIED INTERLEUKIN 2 FOR TREATING RESPIRATORY DISEASE

(71) Applicant: Yanhui Xie, Shanghai (CN)

(72) Inventors: Yanhui Xie, Shanghai (CN); Kefei Wu, Fuzhou (CN); Jiexian Ma, Shanghai (CN)

(73) Assignee: Yanhui Xie, Shanghai (CN)

( * ) Notice: Subject to any disclaimer, the term of this patent is extended or adjusted under 35 U.S.C. 154(b) by 0 days.

(21) Appl. No.: 16/084,952

(22) PCT Filed: Mar. 16, 2016

(86) PCT No.: PCT/CN2016/076441
§ 371 (c)(1),
(2) Date: Sep. 13, 2018

(87) PCT Pub. No.: WO2017/156720
PCT Pub. Date: Sep. 21, 2017

(65) Prior Publication Data
US 2019/0083635 A1  Mar. 21, 2019

(51) Int. Cl.
| | | |
|---|---|---|
| *A61K 38/20* | (2006.01) | |
| *A61K 47/60* | (2017.01) | |
| *A61K 31/573* | (2006.01) | |
| *A61K 38/22* | (2006.01) | |
| *A61P 11/06* | (2006.01) | |
| *A61K 9/00* | (2006.01) | |
| *A61K 31/58* | (2006.01) | |

(52) U.S. Cl.
CPC .............. *A61K 47/60* (2017.08); *A61K 9/008* (2013.01); *A61K 9/0043* (2013.01); *A61K 9/0075* (2013.01); *A61K 31/573* (2013.01); *A61K 31/58* (2013.01); *A61K 38/20* (2013.01); *A61K 38/2013* (2013.01); *A61K 38/22* (2013.01); *A61P 11/06* (2018.01)

(58) Field of Classification Search
CPC ........................... A61K 47/60; A61K 38/2013
See application file for complete search history.

(56) References Cited

U.S. PATENT DOCUMENTS

| | | | |
|---|---|---|---|
| 6,706,289 B2 | 3/2004 | Lewis et al. | |
| 2004/0185103 A1 | 9/2004 | Lewis et al. | |
| 2005/0036951 A1* | 2/2005 | Henderson | A61K 9/0073 424/46 |

FOREIGN PATENT DOCUMENTS

| | | |
|---|---|---|
| CN | 1507357 A | 6/2004 |
| CN | 101897954 A | 12/2010 |
| CN | 102 764 429 A | 11/2012 |
| GB | 2 189 393 A | 10/1987 |
| JP | 2004-534721 A | 11/2004 |
| WO | WO 02/36169 A2 | 5/2002 |

OTHER PUBLICATIONS

Cetinkaya, et al; A comparison of nebulized budesonide, and intramuscular, and oral dexamehtasone, for treatment of croup; Int. Pediatr Otorhinolaryngol 2004; 68(4):453-6.
Chen, et al; GLucocorticoid amplifies IL-2-dependent expansion of functional FoxP3 +CD4+CD25+ T regulatory cell in vivo etc.; Eur. J. Immunol; 2006; 36:2139-2149.
Fehervari, et al; Development and function of CD25+ regulatory T cells; Curr Opin Immunol; 2004; 16(2):203-208.
Fishburn; The Pharmacology of PEGylation: Balancing PD with PK to Generate Novel Therapeutics; J Pharm Sci; 2008; 97(10):4167-83.
Fontenot, et al; Foxp3 programs the development and function of CD4+CD25+regulatory T cells; Nat Immunol; 2003; 4(4):330-6.
Gupta, et al; International trends in admissions and drug sales for asthma; Int J Tuberc Lung Dis; 2006; 10(2):138-45.
Holgate; The epidemic of asthma and allergy; J R Soc Med; 2004; 97 (3):103-10.
Jeffery, et al; 1,25-dihydroxyvitamin D3, and interleukin-2 combine to inhibit T cell production of inflammatory cytokines, etc.; J Immunol; 2009;183(9):5458-67.
Kearley, et al; Resolution of airway inflammation and hyperreactivity after in vivo transfer of CD4+CD25+ regulatory T cells etc.; J Exp Med; 2005;202:1539-47.
Ma, et al; Alleviating allergic airway diseases by means of short-term admin of IL-2 and dexamethasone; J Allergy Clin Immunol; 2011; 127(6):1447-56.e6.
Robinson; The role of T cell in asthma; J Allergy Clin Immunol; 2010; 126(6):1081-91.
Robinson; Regulatory T cells and asthma; Clin Exp Allergy; 2009; 39(9):1314-23.
Shi, et al; An increased ratio of Th2/Treg cells in patients with moderate to severe asthma; Chin Med J; 2013; 126(12):2248-53.
Stelmaszczyk-Emmel, et al; Frequency and Activation of CD4+ CD25high FoxP3 +Regulatory T Cells in Peripheral Blood etc.; Int Arch Allergy Immunol; 2013;162(1):16-24.
Thornton, et al; Spatiotemporally separated antigen uptake by alveolar dendritic cells and airway presentation etc.; J Exp Med; 2012;209(6):1183-99.
Vignali, et al; How regulatory T cells work; Nat. Rev Immunol; 2008; 8(7):523-32.
Wilson, et al; Suppression of Murine Allergic Airway Disease by IL-2:Anti-IL-2 Monoclonal Antibody-Induced Regulatory T Cells; J Immunol; 2008; 181(10):6942-54.
Ma, Jiexian; To Alleviate Airway Allergic Inflammation Diseases as well as Mechanisms by IL-2 Combined with Dexamethasone; China Master's Theses; Dec. 15, 2009 (Abstract incl).

(Continued)

*Primary Examiner* — Prema M Mertz
(74) *Attorney, Agent, or Firm* — Kilpatrick, Townsend & Stockton LLP

(57) ABSTRACT

The present invention provides an inhalable pharmaceutical composition comprising a glucocorticoid and a polyethylene glycol (PEG)-modified interleukin-2 for treating a respiratory disease. The invention further provides an application of a PEG-modified interleukin-2 for preparing a pharmaceutical composition for enhancing the efficacy of a glucocorticoid in treating the respiratory disease. The invention also provides a method for treating the respiratory disease.

17 Claims, 11 Drawing Sheets
Specification includes a Sequence Listing.

(56) References Cited

OTHER PUBLICATIONS

ISA, State Intellectual Property Office of P.R. China; International Search Report dated Dec. 15, 2016 for PCT/CN2016/076441.
Jiexian Ma, et al; Alleviating allergic airway diseases by means of short-term administration of IL-2 and dexamethasone; J.Allergy Clin Immuno.; Mar. 4, 2011; vol. 127, No. 6.
Kefei Wu, et al; Short-term intratracheal use of PEG-modified IL-2 and glucocorticoid persistently alleviates asthma in a mouse model; Scientific Reprts; Aug. 16, 2016; 6:31562.
European Patent Office; Communication and Extended European Search Report dated Dec. 16, 2019 of Appl. No. 16893885.0.
Japanese Patent Office; Official Action dated Sep. 3, 2019; Japanese Patent Appl. No. 2018-548897.
Jiexian Ma, et al; Alleviating allergic airway diseases by means of short-term administration of IL-2 and dexamethasone; J.Allergy Clin Immuno.; Jun. 2011; vol. 127, No. 6.

* cited by examiner

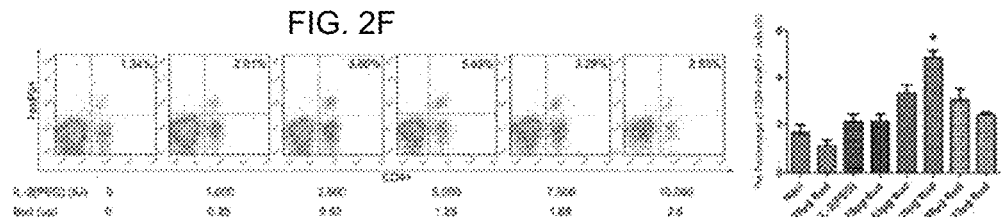
FIG. 2F
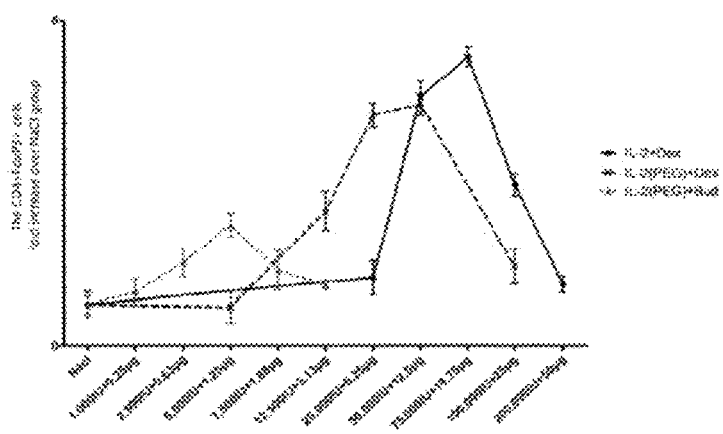
FIG. 2G
FIG. 2H
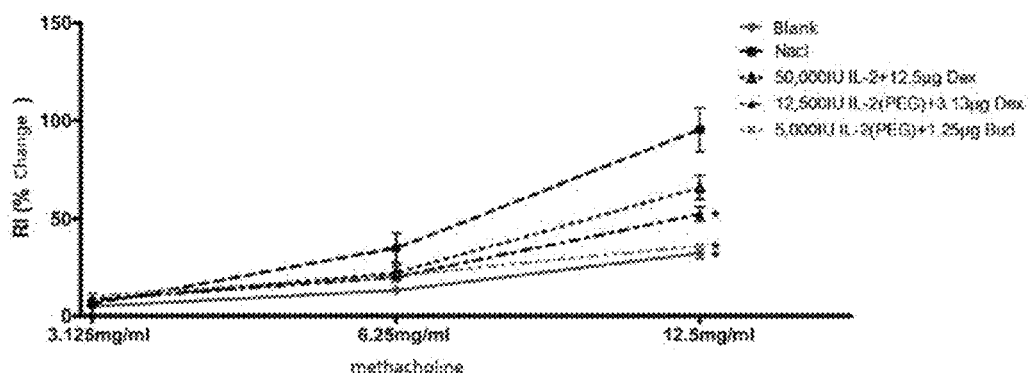
FIG. 2I
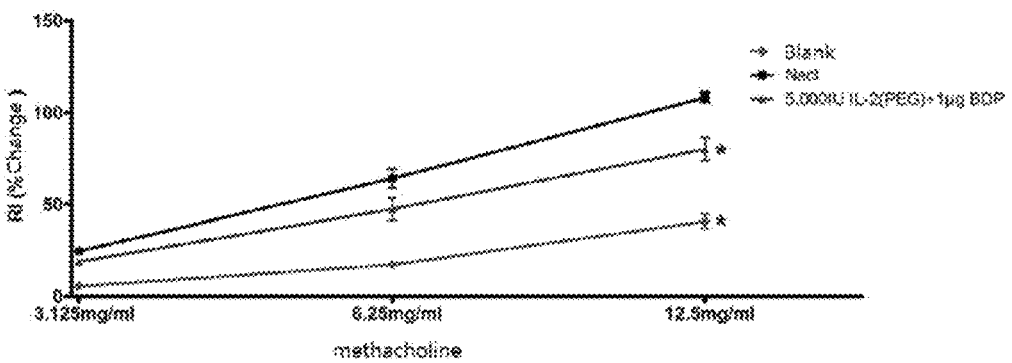

GLUCOCORTICOID COMBINED WITH POLYETHYLENE GLYCOL-MODIFIED INTERLEUKIN 2 FOR TREATING RESPIRATORY DISEASE

CROSS-REFERENCE TO RELATED APPLICATIONS

The present application is a 371 National Phase application of PCT/CN2016/076441, filed Mar. 16, 2016, the disclosure of which is hereby incorporated by reference in its entirety for all purposes.

TECHNICAL FIELD

The present invention relates to a pharmaceutical composition for treating a respiratory disease, in particular to an inhalable pharmaceutical composition of a glucocorticoid and a polyethylene glycol (PEG)-modified interleukin 2 (IL-2), and the present invention also relates to use of a polyethylene glycol-modified interleukin 2 for preparing a pharmaceutical composition for enhancing the therapeutic efficacy of a glucocorticoid on a respiratory disease, and a method for treating a respiratory disease.

BACKGROUND ART

With the change of living environment and the increasing accessible allergens, the incidence rate of respiratory allergic diseases including asthma is increased year by year, causing great economic burden for developing and developed countries, and asthma has a hazard to all ages and genders, and has a certain mortality rate, making its prevention and treatment as a public health and clinical issue of great concern[1, 2].

In the pathological process of asthma, allergens are presented by antigen presenting cells (APCs) to naïve CD4+T cells in lymph nodes, further inducing the differentiation of these naïve CD4+ T cells into effector T cells Th2 type, which secrete a variety of cytokines (IL-4, IL-5, IL-13, etc.) that can promote the accumulation of eosinophils to inflammation sites, promote the secretion of mucus by glands, and promote the secretion of IgE by activated B lymphocytes, the IgE binds to the surface of mastocytes, and after the allergens re-enter into the body, they cross-link with the IgE bound to the surface of mastocytes, which stimulates the mastocytes to secrete a series of contents that cause respiratory hyperreaction. The long-term diseased population suffers from changes in tissue morphology, airway remodeling, and formation of irreversible airway stenosis[3]. At present, drugs with the effect of relaxing airway smooth muscle and dilating the trachea combined with glucocorticoids are mainly used in clinical practice for asthma control, which require multiple daily and long-term administrations, have obvious side effects and are easy to produce drug resistance.

Regulatory T cells are divided into natural regulatory T cells (nTreg) derived from thymus and inducible regulatory T cells (iTreg) differentiated from Th0 under a certain intensity of antigen stimulation, and these regulatory T cells play an immune-modulatory role and protect the body from damage by the autoimmune system through the killing effect by direct contact with effector T cells, or secretion of anti-inflammatory factors including IL-10 and TGF-β, etc. [3-5]. In the pathogenesis of asthma, Treg plays an important role in immune regulation through a variety of mechanisms [6]. At present, there is evidence showing that the imbalance between Th2 cells and Treg cells in the body is an important mechanism leading to the pathogenesis of asthma[1], and in a number of studies on asthma patients, the ratio of Th2/Treg was found to be closely related to the severity and remission of asthma[7, 8].

As a global disease control and treatment problem, the traditional treatment methods of asthma have their limitations and side effects, so far, there has not been a treatment method that achieves long-term control of chronic airway inflammation in asthma and thus inhibits airway remodeling via a short-term administration. A number of studies have recently achieved the goal of controlling and treating asthma by using 1,25-(OH)$_2$ VitD3[9], IL-2/anti-IL-2[10], steroid drugs[11] or direct infusion of Treg[12] to upregulate the Treg in the body. Compared with traditional treatment methods, the methods for treating asthma by upregulating Treg is to treat the disease from the pathogenesis of asthma, which have less administration times and relatively long duration of curative effect, however, some of these methods can only be used to prevent the onset of asthma, and some are difficult to perform in general treatments, and at the same time, the upregulation effect of these methods on Treg is still not ideal, and their long-term use still has certain side effects. In our previous study, it has been shown that intraperitoneal injection of a glucocorticoid (Dex) combined with interleukin 2 can effectively upregulate the ratio of Treg in the body for a long time, and relieve asthma symptoms, and its upregulation mechanism was explored[13]. However, this systemic treatment, upregulating Treg and relieving symptoms, also changes the ratio of Th2/Treg that it should have, breaks the immune balance, and has potential disadvantages; and the dose is relatively large, which exceeds the dose to be tolerated by humans; and the in vivo administration of such a large dose of interleukin 2 may cause fever, rigor, hematopoiesis inhibition, and severe leakage syndrome, which is particularly difficult for asthma patients to tolerate.

The preconditions for that the local administration can exert effects include that enriched drug is capable of closely contacting target cells locally. Studies have shown that the presentation of antigen, and the enrichment and continuous activation of T cells at an inflammation site are all completed in the airway[14]. Therefore, the drug inhaled to the respiratory tract through atomization can bind to and act on an immune-modulatory target in the respiratory tract.

SUMMARY OF THE INVENTION

The present invention provides a method of local administration through atomization in the respiratory tract, and proves that by this convenient and non-invasive method, Treg can be locally upregulated with a drug at a small dose to achieve the purpose of effectively alleviating asthma for a long time.

In the first aspect, the present invention provides an inhalable pharmaceutical composition comprising a polyethylene glycol (PEG)-modified interleukin 2 and a glucocorticoid, and optionally a pharmaceutically acceptable carrier and/or excipient.

In one embodiment, the glucocorticoid is one or more selected from the group consisting of dexamethasone (Dex), budesonide (Bud), beclomethasone dipropionate (BDP), ciclesonide, hydrocortisone, cortisone, prednison, prednisolone, methylprednisolone, triamcinolone, betamethasone, clobetasone butyrate, triamcinolone acetonide, fluocinolone acetonide, mometasone furoate, halcinonide, clobetasol propionate, halcinonide, halometasone monohydrate, and diflorasone diacetate, preferably the glucocorticoid is one or more selected from the group consisting of dexamethasone, budesonide and beclomethasone dipropionate, preferably the glucocorticoid comprises dexamethasone, budesonide and beclomethasone dipropionate, and preferably the glucocorticoid is a combination of dexamethasone, budesonide and beclomethasone dipropionate.

In another embodiment, the interleukin 2 (IL-2) is a human-derived IL-2, for example as set forth in SEQ ID NO. 1.

In another embodiment, the PEG modification is a modification with a non-branched PEG or a branched PEG, such as a modification with a non-branched PEG or a branched PEG with a molecular weight of 2-60 KD, preferably a modification with a non-branched PEG or a branched PEG with a molecular weight of 2, 4, 6, 8, 10, 20, 30, 40, 50 or 60 KD, and preferably a modification with a non-branched PEG with a molecular weight of 10 or 20 KD or a branched PEG with a molecular weight of 20 KD. The PEG modification according to the invention can be at any site in IL-2 suitable to be PEG modified, e.g. at residue lysine, serine, threonine or N-terminal alpha-amino of IL-2. In one embodiment, the PEG modification is at the N-terminal amino acid residue of IL-2, e.g. N-terminal lysine, serine or threonine of IL-2. In one embodiment, the PEG modification is at the N-terminal alpha-amino of IL-2. The PEG modification may be a single-site or multiple-site modification.

In another embodiment, the pharmaceutical composition of the present invention is formulated in a form of dry powder composition, and optionally comprises one or more suitable diluents or carriers such as lactose, dextran, mannitol or glucose, and preferably α-lactose monohydrate.

In another embodiment, the pharmaceutical composition of the present invention is formulated in a form of a pressurized metered dose inhalation, and both the PEG-modified IL-2 (IL-2(PEG)) and the glucocorticoid are suspended or completely dissolved in a liquid propellant mixture.

In another embodiment, the ratio of the PEG-modified IL-2 to the glucocorticoid is between 1,000 IU IL-2(PEG): 1 μg glucocorticoid and 10,000 IU IL-2(PEG): 1 μg glucocorticoid. For example, the ratio of the IL-2(PEG) to the glucocorticoid is 1,000 IU IL-2(PEG): 1 μg glucocorticoid; 2,000 IU IL-2(PEG):1 μg glucocorticoid; 3,000 IU IL-2 (PEG):1 μg glucocorticoid or 4,000 IU IL-2(PEG):1 μg glucocorticoid; 5,000 IU IL-2(PEG):1 μg glucocorticoid; 6,000 IU IL-2(PEG):1 μg glucocorticoid; 7,000 IU IL-2 (PEG):1 μg glucocorticoid; 8,000 IU IL-2(PEG):1 μg glucocorticoid; 9,000 IU IL-2(PEG):1 μg glucocorticoid or 10,000 IU IL-2(PEG):1 μg glucocorticoid. Preferably the ratio of IL-2(PEG) to the glucocorticoid is 3,000 IU IL-2 (PEG):1 μg glucocorticoid; 4,000 IU IL-2(PEG):1 μg glucocorticoid; 5,000 IU IL-2(PEG):1 μg glucocorticoid or 6,000 IU IL-2(PEG):1 μg glucocorticoid.

In another embodiment, the dose of the PEG-modified IL-2 is between 3,000 IU and 100,000 IU, preferably between 5,000 IU and 50,000 IU. For example, the dose of the PEG-modified IL-2 can be 3,000 IU, 4,000 IU, 5,000 IU, 6,000 IU, 7,000 IU, 8,000 IU, 9,000 IU, 10,000 IU, 11,000 IU, 12,000 IU, 13,000 IU, 14,000 IU, 15,000 IU, 16,000 IU, 17,000 IU, 18,000 IU, 19,000 IU, 20,000 IU, 25,000 IU, 30,000 IU, 35,000 IU, 40,000 IU, 45,000 IU, 50,000 IU, 60,000 IU, 70,000 IU, 80,000 IU, 90,000 IU or 100,000 IU.

In another embodiment, the glucocorticoid is Dex, preferably the ratio of the PEG-modified IL-2 to Dex is 4,000 IU IL-2 (PEG): 1 μg Dex, and preferably the dose of the PEG-modified IL-2 is between 7,500 IU and 80,000 IU, and more preferably the dose of the PEG-modified IL-2 is between 12,500 IU and 50,000 IU. For example, the dose of the PEG-modified IL-2 can be 7,500 IU, 8,000 IU, 8,500 IU, 9,000 IU, 9,500 IU, 10,000 IU, 10,500 IU, 11,000 IU, 11,500 IU, 12,000 IU, 12,500 IU, 13,000 IU, 13,500 IU, 14,000 IU, 14,500 IU, 15,000 IU, 16,000 IU, 17,000 IU, 18,000 IU, 19,000 IU, 20,000 IU, 25,000 IU, 30,000 IU, 35,000 IU, 40,000 IU, 45,000 IU or 50,000 IU.

In another embodiment, the glucocorticoid is Bud, preferably the ratio of the PEG-modified IL-2 to Bud is 5,000 IU IL-2 (PEG): 1 μg Bud, and preferably the dose of the PEG-modified IL-2 is between 3,500 IU and 80,000 IU, and more preferably the dose of the PEG-modified IL-2 is between 5,000 IU and 50,000 IU. For example, the dose of the PEG-modified IL-2 can be 3,500 IU, 4,000 IU, 4,500 IU, 5,000 IU, 5,500 IU, 6,000 IU, 6,500 IU, 7,000 IU, 7,500 IU, 8,000 IU, 8,500 IU, 9,000 IU, 9,500 IU, 10,000 IU, 10,500 IU, 11,000 IU, 11,500 IU, 12,000 IU, 12,500 IU, 13,000 IU, 13,500 IU, 14,000 IU, 14,500 IU, 15,000 IU, 16,000 IU, 17,000 IU, 18,000 IU, 19,000 IU, 20,000 IU, 25,000 IU, 30,000 IU, 35,000 IU, 40,000 IU, 45,000 IU or 50,000 IU.

In another embodiment, the glucocorticoid is BDP, preferably the ratio of the PEG-modified IL-2 to BDP is 5,000 IU IL-2 (PEG): 1 μg BDP, and preferably the dose of the PEG-modified IL-2 is between 3,500 IU and 80,000 IU, and more preferably the dose of the PEG-modified IL-2 is between 5,000 IU and 50,000 IU. For example, the dose of the PEG-modified IL-2 can be 3,500 IU, 4,000 IU, 4,500 IU, 5,000 IU, 5,500 IU, 6,000 IU, 6,500 IU, 7,000 IU, 7,500 IU, 8,000 IU, 8,500 IU, 9,000 IU, 9,500 IU, 10,000 IU, 10,500 IU, 11,000 IU, 11,500 IU, 12,000 IU, 12,500 IU, 13,000 IU, 13,500 IU, 14,000 IU, 14,500 IU, 15,000 IU, 16,000 IU, 17,000 IU, 18,000 IU, 19,000 IU, 20,000 IU, 25,000 IU, 30,000 IU, 35,000 IU, 40,000 IU, 45,000 IU or 50,000 IU.

In the second aspect, the present invention provides the above pharmaceutical composition for treating a respiratory disease, and preferably the respiratory disease is chronic obstructive pulmonary disease (COPD) or asthma.

In the third aspect, the present invention provides use of a polyethylene glycol-modified interleukin 2 for preparing a pharmaceutical composition for enhancing the therapeutic efficacy of a glucocorticoid on a respiratory disease, wherein the pharmaceutical composition optionally comprises a pharmaceutically acceptable carrier and/or excipient.

In one embodiment, the pharmaceutical composition of the present invention is an inhalable pharmaceutical composition.

In another embodiment, the respiratory disease of the present invention is chronic obstructive pulmonary disease (COPD) or asthma.

In another embodiment, the pharmaceutical composition comprises a glucocorticoid.

In another embodiment, the glucocorticoid of the present invention is one or more selected from the group consisting of dexamethasone (Dex), budesonide (Bud), beclomethasone dipropionate (BDP), ciclesonide, hydrocortisone, cortisone, prednison, prednisolone, methylprednisolone, triamcinolone, betamethasone, clobetasone butyrate, triamcinolone acetonide, fluocinolone acetonide, mometasone furoate, halcinonide, clobetasol propionate, halcinonide, halometasone monohydrate and diflorasone diacetate, and preferably the glucocorticoid is one or more selected from the group consisting of dexamethasone, budesonide and beclomethasone dipropionate, and preferably the glucocorticoid comprises dexamethasone, budesonide and beclomethasone dipropionate.

In another embodiment, the interleukin 2 (IL-2) is a human-derived IL-2, for example as set forth in SEQ ID NO. 1.

In another embodiment, the PEG modification is a modification with a non-branched PEG or a branched PEG, such as a modification with a non-branched PEG or a branched PEG with a molecular weight of 2-60 KD, preferably a modification with a non-branched PEG or a branched PEG with a molecular weight of 2, 4, 6, 8, 10, 20, 30, 40, 50 or 60 KD, and preferably a modification with a non-branched PEG with a molecular weight of 10 or 20 KD or a branched PEG with a molecular weight of 20 KD. The PEG modification according to the invention can be at any site in IL-2 suitable to be PEG modified, e.g. at residue lysine, serine, threonine or the N-terminal alpha-amino of IL-2. In one embodiment, the PEG modification is at the N-terminal amino acid residue of IL-2, e.g. N-terminal lysine, serine or threonine of IL-2. In one embodiment, the PEG modification is at the N-terminal alpha-amino of IL-2. The PEG modification may be a single-site or multiple-site modification.

In another embodiment, the pharmaceutical composition of the present invention is formulated in a form of dry powder composition, and optionally comprises one or more suitable diluents or carriers such as lactose, dextran, mannitol or glucose, and preferably α-lactose monohydrate.

In another embodiment, the pharmaceutical composition of the present invention is formulated in a form of a pressurized metered dose inhalation, and both the PEG-modified IL-2 and glucocorticoid are suspended or completely dissolved in a liquid propellant mixture.

In another embodiment, the ratio of the PEG-modified IL-2 to the glucocorticoid is between 1,000 IU IL-2(PEG): 1 µg glucocorticoid and 10,000 IU IL-2(PEG): 1 µg glucocorticoid. For example, the ratio of the IL-2(PEG) to the glucocorticoid is 1,000 IU IL-2(PEG): 1 µg glucocorticoid; 2,000 IU IL-2(PEG):1 µg glucocorticoid; 3,000 IU IL-2(PEG):1 µg glucocorticoid or 4,000 IU IL-2(PEG):1 µg glucocorticoid; 5,000 IU IL-2(PEG):1 µg glucocorticoid; 6,000 IU IL-2(PEG):1 µg glucocorticoid; 7,000 IU IL-2(PEG):1 µg glucocorticoid; 8,000 IU IL-2(PEG):1 µg glucocorticoid; 9,000 IU IL-2(PEG):1 µg glucocorticoid or 10,000 IU IL-2(PEG):1 µg glucocorticoid. Preferably the ratio of IL-2(PEG) to the glucocorticoid is 3,000 IU IL-2(PEG):1 µg glucocorticoid; 4,000 IU IL-2(PEG):1 µg glucocorticoid; 5,000 IU IL-2(PEG):1 µg glucocorticoid or 6,000 IU IL-2(PEG):1 µg glucocorticoid.

In another embodiment, the dose of the PEG-modified IL-2 is between 3,000 IU and 100,000 IU, preferably between 5,000 IU and 50,000 IU. For example, the dose of the PEG-modified IL-2 can be 3,000 IU, 4,000 IU, 5,000 IU, 6,000 IU, 7,000 IU, 8,000 IU, 9,000 IU, 10,000 IU, 11,000 IU, 12,000 IU, 13,000 IU, 14,000 IU, 15,000 IU, 16,000 IU, 17,000 IU, 18,000 IU, 19,000 IU, 20,000 IU, 25,000 IU, 30,000 IU, 35,000 IU, 40,000 IU, 45,000 IU, 50,000 IU, 60,000 IU, 70,000 IU, 80,000 IU, 90,000 IU or 100,000 IU.

In another embodiment, the glucocorticoid is Dex, preferably the ratio of the PEG-modified IL-2 to Dex is 4,000 IU IL-2(PEG): 1 µg Dex, and preferably the dose of the PEG-modified IL-2 is between 7,500 IU and 80,000 IU, and more preferably the dose of the PEG-modified IL-2 is between 12,500 IU and 50,000 IU. For example, the dose of the PEG-modified IL-2 can be 7,500 IU, 8,000 IU, 8,500 IU, 9,000 IU, 9,500 IU, 10,000 IU, 10,500 IU, 11,000 IU, 11,500 IU, 12,000 IU, 12,500 IU, 13,000 IU, 13,500 IU, 14,000 IU, 14,500 IU, 15,000 IU, 16,000 IU, 17,000 IU, 18,000 IU, 19,000 IU, 20,000 IU, 25,000 IU, 30,000 IU, 35,000 IU, 40,000 IU, 45,000 IU or 50,000 IU.

In another embodiment, the glucocorticoid is Bud, preferably the ratio of the PEG-modified IL-2 to Bud is 5,000 IU IL-2(PEG): 1 µg Bud, and preferably the dose of the PEG-modified IL-2 is between 3,500 IU and 80,000 IU, and more preferably the dose of the PEG-modified IL-2 is between 5,000 IU and 50,000 IU. For example, the dose of the PEG-modified IL-2 can be 3,500 IU, 4,000 IU, 4,500 IU, 5,000 IU, 5,500 IU, 6,000 IU, 6,500 IU, 7,000 IU, 7,500 IU, 8,000 IU, 8,500 IU, 9,000 IU, 9,500 IU, 10,000 IU, 10,500 IU, 11,000 IU, 11,500 IU, 12,000 IU, 12,500 IU, 13,000 IU, 13,500 IU, 14,000 IU, 14,500 IU, 15,000 IU, 16,000 IU, 17,000 IU, 18,000 IU, 19,000 IU, 20,000 IU, 25,000 IU, 30,000 IU, 35,000 IU, 40,000 IU, 45,000 IU or 50,000 IU.

In another embodiment, the glucocorticoid is BDP, preferably the ratio of the PEG-modified IL-2 to BDP is 5,000 IU IL-2(PEG): 1 µBDP, and preferably the dose of the PEG-modified IL-2 is between 3,500 IU and 80,000 IU, and more preferably the dose of the PEG-modified IL-2 is between 5,000 IU and 50,000 IU. For example, the dose of the PEG-modified IL-2 can be 3,500 IU, 4,000 IU, 4,500 IU, 5,000 IU, 5,500 IU, 6,000 IU, 6,500 IU, 7,000 IU, 7,500 IU, 8,000 IU, 8,500 IU, 9,000 IU, 9,500 IU, 10,000 IU, 10,500 IU, 11,000 IU, 11,500 IU, 12,000 IU, 12,500 IU, 13,000 IU, 13,500 IU, 14,000 IU, 14,500 IU, 15,000 IU, 16,000 IU, 17,000 IU, 18,000 IU, 19,000 IU, 20,000 IU, 25,000 IU, 30,000 IU, 35,000 IU, 40,000 IU, 45,000 IU or 50,000 IU.

In the fourth aspect, the present invention provides a method for treating a respiratory disease, characterized in administering a patient a therapeutically effective amount of the polyethylene glycol-modified interleukin 2 and the glucocorticoid of the present invention by inhalation, for example, administering the pharmaceutical composition of the present invention.

In one embodiment, the administration according to the present invention is through oral or intranasal inhalation, preferably by means of an aerosol or a spray.

In another embodiment, the respiratory disease of the present invention is chronic obstructive pulmonary disease (COPD) or asthma.

In the fifth aspect, the present invention provides a method for preparing the pharmaceutical composition of the present invention.

The present invention demonstrated that, compared with a glucocorticoid alone, a glucocorticoid in combination with IL-2 take effect faster. Compared with systemic administration, short-term local application of a glucocorticoid in combination with IL-2 in the respiratory tract can upregulate Treg at a low dose without affecting other immune systems of the body, and successfully relieve asthma symptoms for at least 6 weeks, indicating that the regular use of the method is expected to solve the problems of chronic airway inflammation and airway remodeling in asthma, and further to cure asthma. Due to the different dosage forms of IL-2 and IL-2(PEG), the metabolism rate of the latter is significantly lowered than that of the former, and the drug can act locally for a longer period of time, and after changing the dosage form, the required dose to achieve the upregulation effect is significantly reduced. The use of a dosage form such as IL-2(PEG):Bud, IL-2(PEG):BDP and the like can further reduce the dose of administration to a range safe and suitable for human. The Tregs produced by the combination of drugs are mainly non-specific Tregs, which can assist the body in combating the airway hypersensitivity reaction caused by various allergens. This novel asthma treatment method, which is non-invasive, convenient, quick-acting, and long-lasting, can definitely bring great benefits to patients in clinic.

BRIEF DESCRIPTION OF THE DRAWINGS

FIG. 1A: modeling and medication time points. FIG. 1B: flow cytometry of Treg in bronchoalveolar lavage fluid of the control, Dex alone, IL-2 alone and combination medication. FIG. 1C: images of lung pathological sections (with 20-fold microscope), H&E staining. Data are expressed as mean±standard deviation (n=6 to 8 per group). *group vs NaCl group, P<0.05. i.p: intraperitoneal injection of OVA antigen for sensitization; i.n: nasal instillation of OVA antigen for challenge.

FIGS. 2A-2I: Study of the optimal dosage form of the drug with a fixed ratio. FIG. 2A: Treg upregulation after using IL-2: Dex at a constant ratio and different doses. FIG. 2B: gel electrophoresis image of IL-2 before and after modified with 20 KD non-branched PEG. FIG. 2C: high performance liquid phase size exclusion chromatography (HP-SEC) detection of IL-2(PEG) stock solution after purification. FIG. 2D: activity detection of PEG-IL-2 (i.e. IL-2 (PEG)). FIG. 2E: Treg upregulation after using IL-2(PEG): Dex at a constant ratio and different doses. FIG. 2F: Treg upregulation after using IL-2(PEG):Bud at a constant ratio and different doses. FIG. 2G: comparison of Treg upregulation of three dosage forms of IL-2: Dex, IL-2(PEG):Dex and IL-2(PEG):Bud. FIG. 2H: lung function measurement after treatment with three dosage forms of IL-2: Dex, IL-2(PEG):Dex and IL-2(PEG):Bud. FIG. 2I: lung function measurement after treatment with IL-2(PEG):BDP. Data are expressed as mean±standard deviation (Treg measurement: n=6 to 8 per group; lung function: n=3 per group), *group vs NaCl group P<0.05.

FIG. 4A: upregulation level of Treg in bronchoalveolar lavage fluid. FIG. 4B: lung function measurement after treatment with IL-2(PEG) alone, Bud alone and combination medication at different doses. FIG. 4C: images of lung pathological sections (under a 20-fold microscope), left: H&E staining; right: PAS staining. Data are expressed as mean±standard deviation (Treg measurement: n=6 per group; lung function: n=3 per group). FIG. 4D: lung function measurement after treatment with combination medication of 10 KD non-branched PEG-modified IL-2 or 20 KD branched PEG-modified IL-2 and Bud. *group vs NaCl group P<0.05.

FIG. 5A: modeling and medication time points. FIG. 5B: lung function measurement after 3, 5, and 7 days of treatment with intraperitoneal injection of dexamethasone (40 μg) and after three days of treatment with local medication of IL-2(PEG):Bud. FIG. 5C: images of lung pathological sections (under a 20-fold microscope), left: H&E staining; right: PAS staining. Data are expressed as mean±standard deviation (n=3 per group). *group vs NaCl group P<0.05.

FIG 6A: modeling and medication time points. FIG. 6B: lung function measurement after 6 weeks of medication. FIG. 6C: images of lung pathological sections (under a 20-fold microscope), left: H&E staining; right: PAS staining. Data are expressed as mean±standard deviation (n=4 per group). *group vs NaCl group P<0.05.

FIG. 7A: flow cytometry of Th2 cells. FIG. 7B: detection of cytokines. Data are expressed as mean±standard deviation (n=6 per group). *group vs NaCl group P<0.05.

FIG. 8A: inhibitory effects of iTreg and nTreg in spleen on spleen lymphopoiesis of DO10.11 mice stimulated by OVA (OVA antigen-specific TCR transgenic mice). FIG. 8B: inhibitory effects of iTreg and nTreg in spleen on lymphopoiesis in spleen lymphocyte mixed reaction system of BALB/c and C57 mice. Data are expressed as mean±standard deviation (n=6 per group). *group vs control group P<0.05.

FIG. 9A: flow cytometry of Th2 and Treg in spleen cells, and FIG. 9B: measurement of cytokines in serum. Data are expressed as mean±standard deviation (n=6 per group).

DETAILED DESCRIPTION OF THE INVENTION

Figure 1A:
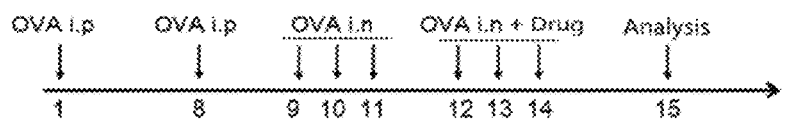
FIGS. 1A-1C: Evaluation of efficacy of local medication.

The present invention is not limited to the specific methods, embodiments, reagents and the like described herein, as these may vary and be modified. The terms used herein are for the purpose to describe particular embodiments but not to limit the scope of the present invention. Unless otherwise defined, all technical and scientific terms used herein have the same meanings as commonly understood by a person skilled in the art.

Before describing in detail the exemplary embodiments of the present invention, definitions are given for the terms that are important for the understanding of the present invention.

The "glucocorticoid" according to the present invention may be any synthetic or naturally occurring glucocorticoid. The glucocorticoid which can be used in the present invention is, for example, a glucocorticoid which is useful for treating respiratory diseases, and the examples include dexamethasone (Dex), budesonide (Bud), beclomethasone dipropionate (BDP), ciclesonide, hydrocortisone, cortisone, prednison, prednisolone, methylprednisolone, triamcinolone, betamethasone, clobetasone butyrate, triamcinolone acetonide, fluocinolone acetonide, mometasone furoate, halcinonide, clobetasol propionate, halcinonide, halometasone monohydrate, diflorasone diacetate, mometasone, loteprednol, etiprednol, triamcinolone, flunisolide, flumoxonide, rofleponide, butixocort, tipredane, etc.

In the context of the present description, reference to "glucocorticoid", unless otherwise indicated, includes all active salts, solvates or derivatives which may be derived from the glucocorticoid. Examples of possible salts or derivatives of the glucocorticoid include: sodium salt, sulfobenzoate, phosphate, isonicotinate, acetate, propionate, dihydrogen phosphate, palmitate, pivalate, fumarate and pharmaceutically acceptable esters (e.g., C1-C6 alkyl esters). The glucocorticoid and active salts or derivatives thereof may also be in their solvate form, such as in the form of hydrate.

The "IL-2" of the present invention refers to IL-2 of any source, including mammalian sources such as human, mouse, rat, primate, and pig, and may be natural or obtained by recombinant or synthetic techniques, including recombinant IL-2 polypeptides produced by a microbial host. The IL-2 may be or comprise a native polypeptide sequence or may be an active variant of a native IL-2 polypeptide. Preferably, the IL-2 polypeptide or active variant is derived from a human source and comprises a recombinant human IL-2, in particular recombinant human IL-2 produced by a microbial host.

In a preferred embodiment, the present invention employs a human-derived IL-2 or an active variant thereof, more preferably produced recombinantly. The nucleotide and amino acid sequences of the human-derived IL-2 are disclosed, for example, in Genbank ref3558 or P60568, respectively, and for example, the sequence of the human-derived IL-2 used in the present invention is set forth in SEQ ID NO. 1 (5'-APTSSSTKKTQLQLEHLLLDLQMILNGIN-NYKNPKLTRMLTFKFY MPK-KATELKHLQCLEEELKPLEEVLNLAQSKNFHLR-PRDLISNINVIVLELKGSETTFMCEYADETATIVEFLNR-WI TFAQSIISTLT-3'). Unless otherwise stated, the IL-2 used in the present invention is a human-derived IL-2 and is in a substantially pure form, for example, having a purity of 95% or more, and more preferably a purity of 96, 97, 98 or 99%. The IL-2 can be used in the form of a monomer or multimer protein.

The "respiratory tract" of the present invention is the airway which is connected to the alveolus and constitutes the lung. The "respiratory disease" of the present invention means a disease or condition associated with the respiratory system. Examples include, but are not limited to, airway inflammation, allergy, respiratory disorder, cystic fibrosis (CF), allergic rhinitis (AR), acute respiratory distress syndrome (ARDS), chronic obstructive pulmonary disease (COPD), asthma, cancer, pulmonary hypertension, pulmonary inflammation, bronchitis, airway obstruction, bronchoconstriction, microbial and viral infections, such as SARS.

COPD is a chronic disease characterized by airway obstruction and reduced maximal expiratory flow from the lung, manifested as persistent daily symptoms such as short of breath (dyspnea) and limited ability to perform daily activities or exertion. In addition, there is a periodic exacerbation of disease states leading to deterioration of daily symptoms and limitation of activities, and the severity of the worsening symptoms/limitation may also result in hospitalization of patients. In addition, there is a gradual decline in lung function (disease progression) over several years.

Asthma is a chronic disease state characterized by extensive, variable, and reversible airflow obstruction, with symptoms including cough, wheezing, polypnea and/or feeling of tightness in the chest. Asthma attacks are usually caused by exposure to an initiator such as pollen, dust or other allergens which cause airway contraction (bronchoconstriction). It should be understood that an individual having a disease state, such as asthma, may exhibit a disease state without visible symptoms from time to time, or may experience periodic attacks during which exhibits symptoms or may experience an exacerbation or worsening of the disease state.

The "prevention" according to the present invention means a prophylactic treatment performed before the subject suffers from a disease or the disease previously diagnosed is deteriorated, thereby enabling the subject to avoid, prevent or reduce the likelihood of the symptoms or related diseases of the disease. The subject may be a subject with an increased risk of developing a disease or a disease previously diagnosed to be deteriorated.

The "treatment", "therapeutically" or "therapeutic" of the present invention means that a method by which a subject to whom such a treatment method is given exhibits a possible reduction in the symptoms of a disease or other conditions. In the context of the present description, unless specifically stated to the contrary, the term "treatment" is intended to include preventing such periodic attack or exacerbation of an existing disease state. Such treatment may be referred to as "maintenance treatment" or "maintenance therapy". The terms "therapeutic" and "therapeutically" may also be interpreted accordingly.

The term "pharmaceutically acceptable carrier" or "excipient" includes any and all solvents, dispersion media, coatings, antibacterial and antifungal agents, isotonic agents and absorption delaying agents, and the like. The use of such media and agents is well known in the art. The active ingredients used in the present invention, such as the glucocorticoid and the polyethylene glycol-modified interleukin 2, can be used in mixture with one or more pharmaceutically acceptable additives, diluents or carriers. Examples of suitable diluents or carriers include lactose (e.g., monohydrate), dextran, mannitol or glucose.

The pharmaceutical composition of the present invention is suitably administered (e.g., administered locally to the respiratory tract) by inhalation in the form of a solution, suspension, aerosol or dry powder formulation. The administration can be by inhalation through the oral or intranasal, and is preferably by an aerosol or spray consisting of powder or liquid, nasal respirable or inhalable particles. The pharmaceutical composition containing an active ingredient is inhaled by the subject by means of the respiratory or inhalable particles, i.e., by inhalation or nasal administration into the respiratory tract. The formulation may contain liquid or solid particles of a respirable or inhalable pharmaceutical composition, and the particles of the present invention comprise respirable or inhalable particles that are sufficiently small in volume so as to pass through the mouth and throat and continue to enter the bronchi and alveolus after inhalation. The diameter of the particles is generally about 0.05, 0.1, 0.5, 1, 2, 4, 6, 8, or 10 microns. In particular, the respirable or inhalable particles have a diameter of from about 0.5 μm to less than 5 μm. Non-inhalable particles in the aerosol or spray are easily deposited in the throat and swallowed. Therefore, the amount of non-respirable particles in the aerosol should be minimal. As far as nasal application is concerned, the preferred particle size range is about 8, 10, 20, 25, 35, 50, 100, 150, 250, 500 μm (diameter) to ensure its retention in the nasal cavity. Liquid formulation can be sprayed into the respiratory tract (nasal part), especially for newborns and infants.

The active ingredients of the present invention are preferably suitable for administration together or separately with a dry powder inhaler, metered dose inhaler or atomizer. The dry powder inhaler, metered dose inhaler and atomizer are well known and a variety of such devices are available.

The dry powder inhaler can be used to administer an active ingredient alone or in combination with a pharmaceutically acceptable carrier, and in the case of administering an active ingredient in combination with a pharmaceutically acceptable carrier, administer in the form of a finely pulverized powder or an ordered mixture. The dry powder inhaler can be a single dose or multiple doses, and can adopt a dry powder or a capsule containing powder.

The metered dose inhaler can be used to administer an active ingredient dispersed in a suitable propellant with or without an additional excipient (e.g., ethanol), surfactant, lubricant, antioxidant, or stabilizer. Suitable propellant includes a hydrocarbon, chlorofluorocarbon and hydrofluorocarbon (e.g., sevoflurane) propellant, or any mixture of such propellants. Preferred propellant is P134a and P227, each of which may be used alone or in combination with other propellant and/or surfactant and/or other excipient. It is also possible to use an atomized aqueous suspension in the form of a unit-dose or multiple-dose formulation, or preferably a solution with or without suitable pH and/or tension regulators.

When active ingredients each are administered together or separately via an atomizer, they may be in the form of an atomized aqueous suspension or solvent, with or without a suitable pH or tension regulator, in a single-dose or multiple-dose device.

The term "therapeutically effective amount" as used in the present invention refers to an amount of an inhalation formulation containing an amount of a medicament required to provide a therapeutic effect when delivered to a patient, for example, to alleviate, prevent or inhibit a particular condition to be treated. The amount of an active ingredient used in the present invention means a unit dose, unless otherwise specifically defined. The therapeutically effective amount can be delivered by a DPI device with one or more jets. Thus, depending on the nature of the drug and the nature and severity of the disease to be treated, it is necessary to perform one or more jets every few hours every day for days, weeks, months, and the like.

The therapeutically effective amount depends to a large extent on the nature of the drug, the condition of the patient, and the nature and severity of the disease to be treated. The therapeutically effective amount can range from as low as 1 ng/kg, for example, an active substance is used effectively when treating a local disease such as asthma, and up to 10 mg/kg, and more particularly in the range of from 20 ng/kg to 1 mg/kg. The therapeutic dose should be indicated on the package or label in the DPI device.

The present invention accordingly relates to such a multiple-dose inhaler comprising the formulation of the present invention. The multiple-dose inhaler may contain a dry powder reservoir containing tens or even hundreds of therapeutically effective amounts.

The pharmaceutical composition of the present invention can be provided in the form of bulk and unit dose as well as in the form of openable or perforable implant, capsule, blister package or cartridge known in the art. The present invention also provides a kit provided with a delivery device, the pharmaceutical composition of the present invention and optionally another suitable additive, such as another therapeutic compound, excipient, surface active substance (as an ingredient of a therapeutic drug and formulation), antioxidant, flavoring and coloring agent, filler, volatile oil, buffer, dispersant, surface active substance, antioxidant, flavoring agent, expanding agent, propellant, and preservative in separate containers, as well as an instruction for use of the kit's components.

In order to make the technical solutions and advantages of the present invention clear, the embodiments of the present invention will be further described in detail below with reference to the accompanying drawings. It should be understood that the examples and drawings are not to be construed as limiting. A person skilled in the art would envisage further modifications to the principles listed herein.

EXAMPLE

Example 1

Modeling of Asthma Mice

Female BALB/c mice aged 6-8 weeks (purchased from SLAC Laboratory Animal Co., Ltd.) were used for modeling of asthma, which were sensitized by intraperitoneal injection with 100 µg of ovalbumin (OVA) (Sigma) and 2 mg of $Al(OH)_3$ for injection (Sigma) on days 1 and 8, and challenged by daily nasal instillation with 20 µl of 2% OVA on days 9-14 (FIG. 1A).

Example 2

Dexamethasone Combined with IL-2 Upregulated Treg in the Airway and Relieved Respiratory Inflammation Response The asthma mice model of Example 1 were subjected to drug intervention while challenge by nasal instillation on days 12-14. The specific administration method was that the mice were anesthetized with 7% chloral hydrate (Sangon Biotech (Shanghai) Co., Ltd.) and then administrated quantitatively through atomization in the lung using an atomization metered dosing device (MicroSprayer®—Model IA-1B), and the administration volume was fixed at 25 ul/mouse, and the administration dose was adjusted by the level of concentration. On the 15th day, relevant indicators were detected.

Collection of bronchoalveolar lavage fluid. The mice were sacrificed by cervical dislocation. The mice were subjected to bronchoalveolar lavage fluid rinsing with 300 ul of PBS solution through an incision on trachea, and repeated 3 times to obtain about 900 ul of bronchoalveolar lavage fluid. The bronchoalveolar lavage fluid was centrifuged at 2,000 rpm for 5 minutes. The cells were collected for flow cytometry. The IFN-γ, IL-4, IL-10, and IL-13 in the supernatant were measured by using commercial ELISA kit (R&D Corp).

Flow cytometry. Flow cytometry was used to detect Treg in the cells collected from bronchoalveolar lavage fluid and spleen cells, wherein CD4 was labeled with FICT and FoxP3 was labeled with APC (eBioscience). Wherein the CD4 is a cell surface marker and can be directly labeled, and the FoxP3 is an intracellular transcription factor and is labeled after cell perforation for immobilization[15]. When detecting Th2 cells in the spleen, a Per-CP-labeled Gata3 antibody (eBioscience) was used, and the cells were perforated and then labeled. All results were analyzed by FlowJo software (Treestar).

Lung histopathology. The lungs of mice were fixed in 10% formalin, embedded in paraffin, sectioned, stained with H&E (Merck & Co, Inc) and PAS (Sigma), respectively, and examined under a 20-fold microscope.

Figure 1B:
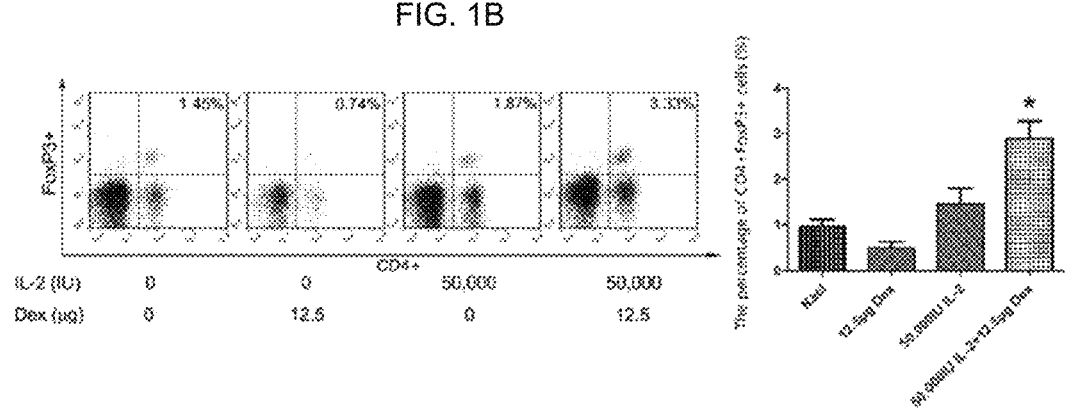
Figure 1C:
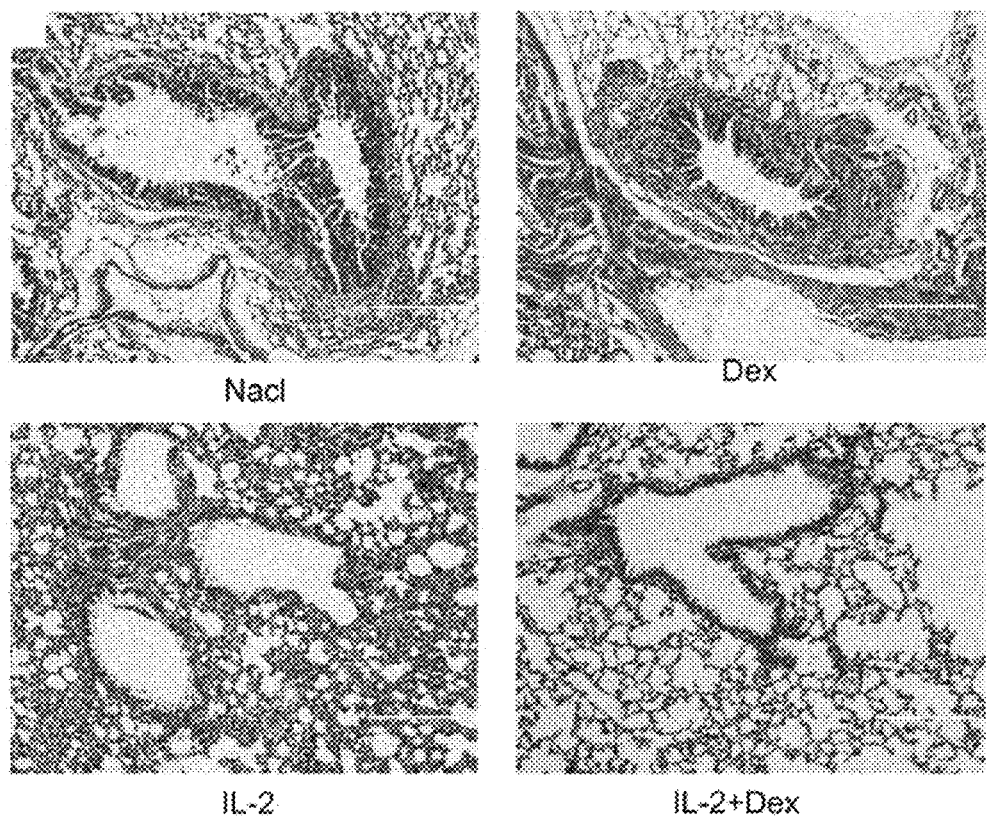

In previous study, 400,000 IU IL-2 in combination with 100 µg dexamethasone, as the optimal dose, could effectively upregulate Treg in the body and alleviate the pathological manifestations of lung tissue in asthma mice[13]. Using the same drug ratio as the previous study (4,000 IU IL-2:1 µg Dex), 50,000 IU IL-2 (Xiamen Amoytop Biotech Co., Ltd.) in combination with 1.25 µg Dex was attempted to treat asthma mice by local administration through atomization in the respiratory tract. It could be observed that Treg in bronchoalveolar lavage fluid was upregulated (p<0.05, FIG. 1B). The lung pathological sections showed that the pathological manifestations of lung inflammation were alleviated. The same effect could not be achieved by using the same dose of any of the drugs alone (FIGs. 1B, 1C), demonstrating that the combination medication was effective and that the effect was not produced by a single drug.

Example 3

Figure 2A:
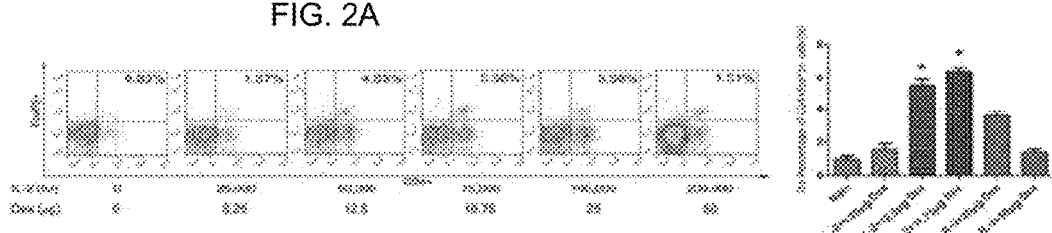

Combination Medication is Dose-Dependent, and the Modified Combination of IL-2(PEG) and Budesonide (Bud) Exerted an Anti-Inflammatory Effect at a Less Dose Considering that the drug has a high concentration in the lungs during local application, an optimal dose is different from that of systemic application, and the previous studies have shown that the combination medication is dose-dependent[13], the dose-dependence and optimal dose of local medication were studied. Modeling was carried out in the same manner as in Example 1, and administration and Treg detection were carried out in the same manner as in Example 2. Within a certain range, as the concentration of the drug increased, the magnitude of Treg upregulation gradually increased, and then the effect began to decrease, which is consistent with the results of previous in vivo studies. Wherein both doses, 50,000 IU IL-2:12.5 μg Dex and 75,000 IU IL-2:18.8 μg Dex, effectively upregulated Treg in the airway ($p<0.05$, FIG. 2A).

Although it can effectively upregulate Treg, the dose, 50,000 IU IL-2, is still relatively large (15 million IU of interleukin 2 is required for an adult of 60 kg). In actual treatment, high dose of IL-2 may cause leakage syndrome and thereby result in an increased risk of pulmonary edema and exacerbation of asthma symptoms, etc., and the combined glucocorticoid also has a relatively high dose, which may similarly lead to adverse reactions caused by the glucocorticoid.

It has been proved that the modification to a macromolecular drug with PEG can not only reduce the antigenicity of the drug, but also prolong the half-life of the drug and increase the residence time of the drug in the body, thereby improving the efficacy of the drug[16]. At present, the clinical application of a PEG-modified drug is generally used to achieve long-term efficacy, but in this experiment, it is to reduce the dose of the drug to one suitable for human use, and is not used to prolong the action time of the drug (this study needs only 3 days). In order to confirm whether the PEG modification method can be used to localize the drug in the airway cavity and reduce its distribution in other tissues, an IL-2 modified with a non-branched PEG of a molecular weight of 20 kD was used to replace the common IL-2 for dose investigation, to achieve a high local concentration in the airway in a short time by utilizing the PEG retention. Unless otherwise specified in the present invention, an IL-2 modified with a non-branched PEG of a molecular weight of 20 kD was used.

Preparation of IL-2(PEG). IL-2 (sequence as set forth in SEQ ID NO. 1), replacing the buffer with an acetic acid-sodium acetate buffer (pH 4~6), was mixed with M-AID-20 kD (Beijing Jenkem Technology Co., Ltd.) non-branched PEG (mass ratio: 1:2~1:6), and the mixture was reduced with sodium cyanoborohydride, and reacted at 2-10° C. for 3-18 hours, to obtain a crude IL-2(PEG). The crude IL-2 (PEG) was initially separated by cation exchange chromatograph with an acetic acid-sodium acetate buffer system. The target protein peak was collected and subjected to reverse phase chromatography, and gradient elution with acetonitrile trifluoroacetic acid system. The target protein peak was collected and concentrated by cation exchange chromatography with an acetic acid-sodium acetate buffer system. The target protein peak was collected, and finally ultrafiltered to be replaced with an acetic acid-sodium acetate buffer to obtain an IL-2(PEG) stock solution.

10 kD non-branched PEG-modified IL-2 and 20 kD branched PEG-modified IL-2 were further prepared, with a process consistent with the preparation of 20 kD non-branched PEG-modified IL-2(PEG).

Figure 2B:
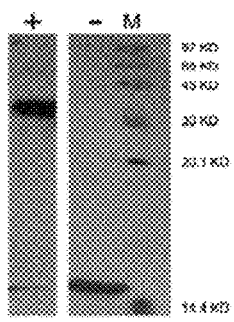
Figure 2C:
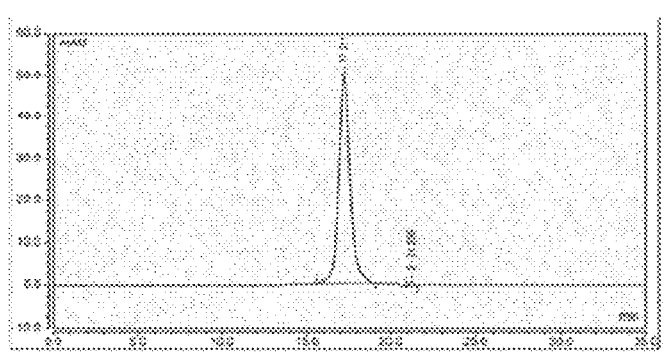
Figure 2D:
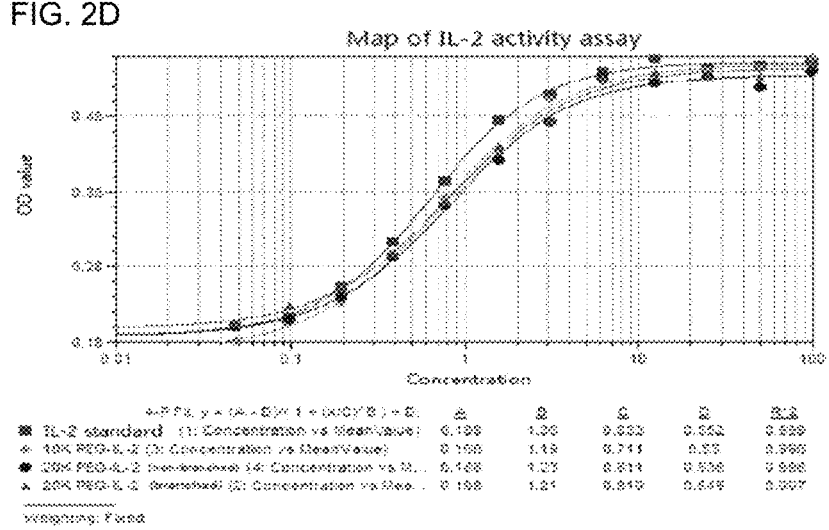

The main modification site by the selected PEG type was the N-terminus of the peptide chain, and after modification with 20 kD non-branched PEG, the IL-2 had a molecular weight of from 15 kD to 35 kD (FIG. 2B) and a high purity (FIG. 2C). Activity was examined by CTLL-2 cell assay and it was confirmed that the PEG-modified IL-2 had an activity comparable to that of the IL-2 working standard (FIG. 2D).

Figure 2E:
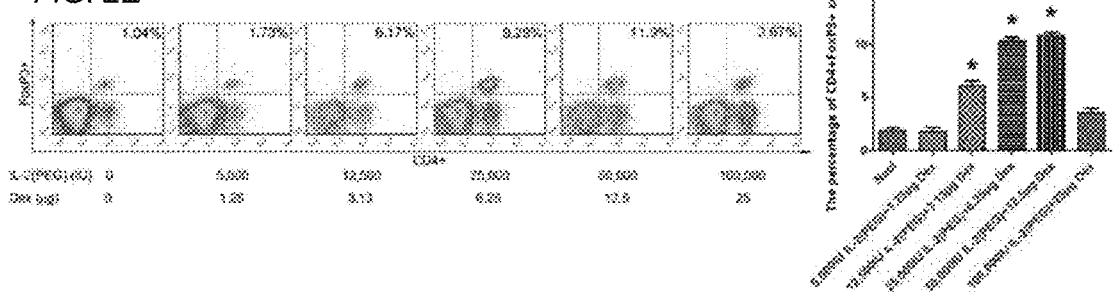

It was unexpectedly discovered that after replacement with IL-2(PEG), the combination medication could play a role in Treg upregulation at a lower dose of IL-2 active unit (12,500 IU IL-2(PEG)+3.13 μg Dex) (FIG. 2E). Since Dex is not a conventional atomization inhaled hormone for asthma treatment, and its molecular particles are not conducive to make the drug to effect locally and easy to enter into the blood, the Dex was replaced with Bud, a clinically common glucocorticoid for local treatment of asthma. It was observed that the onset dose was further decreased to 5,000 IU IL-2(PEG)+1.25 μg Bud (FIG. 2F).

In the comprehensive analysis of Treg upregulation by the three different drug combinations, it could be seen that the magnitude of Treg upregulation was mainly related to the dose of IL-2, when the dose of IL-2 was higher, the magnitude of Treg upregulation was higher, while the modified IL-2(PEG) and the glucocorticoid Bud, that works rapidly and locally in the respiratory tract, helped to reduce the onset concentration (FIG. 2G). The magnitude of upregulation is determined by the IL-2 dose, and the corresponding amount of glucocorticoid is determined by the ratio of the two. The ratio in this experiment was based on previous in vivo drug discovery[13], however, Treg can only be upregulated by the synergistic action of the two drugs. Since Treg plays a role in immune-regulation, and as long as it is up-regulated, an effect can be produced.

Next, the onset doses of the three dosage forms, 50,000 IU IL-2+12.5 μg Dex, 12,500 IU IL-2(PEG)+3.13 μg Dex and 5,000 IU IL-2(PEG)+1.25 μg Bud, were used to treat asthma mice, and the lung function of the mice was measured.

Lung function measurement. After being anesthetized with 2% pentobarbital sodium, the mice were subjected to respiratory provocation test with methacholine (Sigma) at 3.125 mg/ml, 6.25 mg/ml, and 12.5 mg/ml prepared in PBS, respectively. The airway resistance curve was plotted and analyzed (FinePoint NAM). The assay was performed using the BUXCO Airway Resistance and Lung Compliance System (BUXCO Electronics).

It could be observed that although the doses were different and the magnitudes of Treg upregulation were different, an improvement of airway compliance could be observed, and except for the mice in the 50,000 IU IL-2+12.5 μg Dex group, significant differences in the other combinations were observed, and the IL-2(PEG)+Bud dosage form had a more significant effect of improving the airway resistance at a smaller dose ($p<0.05$, FIG. 2H).

In addition, when replaced with BDP, another clinically common glucocorticoid for local treatment of asthma, the 5,000 IU IL-2(PEG)+1 μg BDP dosage form could also significantly improve the airway resistance (*group vs NaCl group, $p<0.05$, FIG. 2I).

Example 4

Optimal Ratio of the New Dosage Form of Combined IL-2 (PEG)+Bud

Although IL-2(PEG)+Bud was effective in upregulating Treg and alleviating asthma, its range of action was narrow (FIG. 2G). Compared with traditional IL-2, IL-2(PEG) has the characteristics of low antigenicity and easy local retention of the drug[16]; and compared with the local medication of Dex in the respiratory tract, Bud has the characteristics of quickly reaching the diseased site and quick onset[17]. In addition, due to changes in the mode of administration, drug concentration and metabolism are different from before. Therefore, there should be a difference in the most suitable dosing ratio of the new dosage form compared to the previous dosage form with the optimal ratio explored by systemic medication. Example 3 proved that IL-2(PEG)+Bud had the optimal effect, but its effective range was narrow, which was inferred to be caused by the inappropriate ratio of the drugs.

Figure 3:
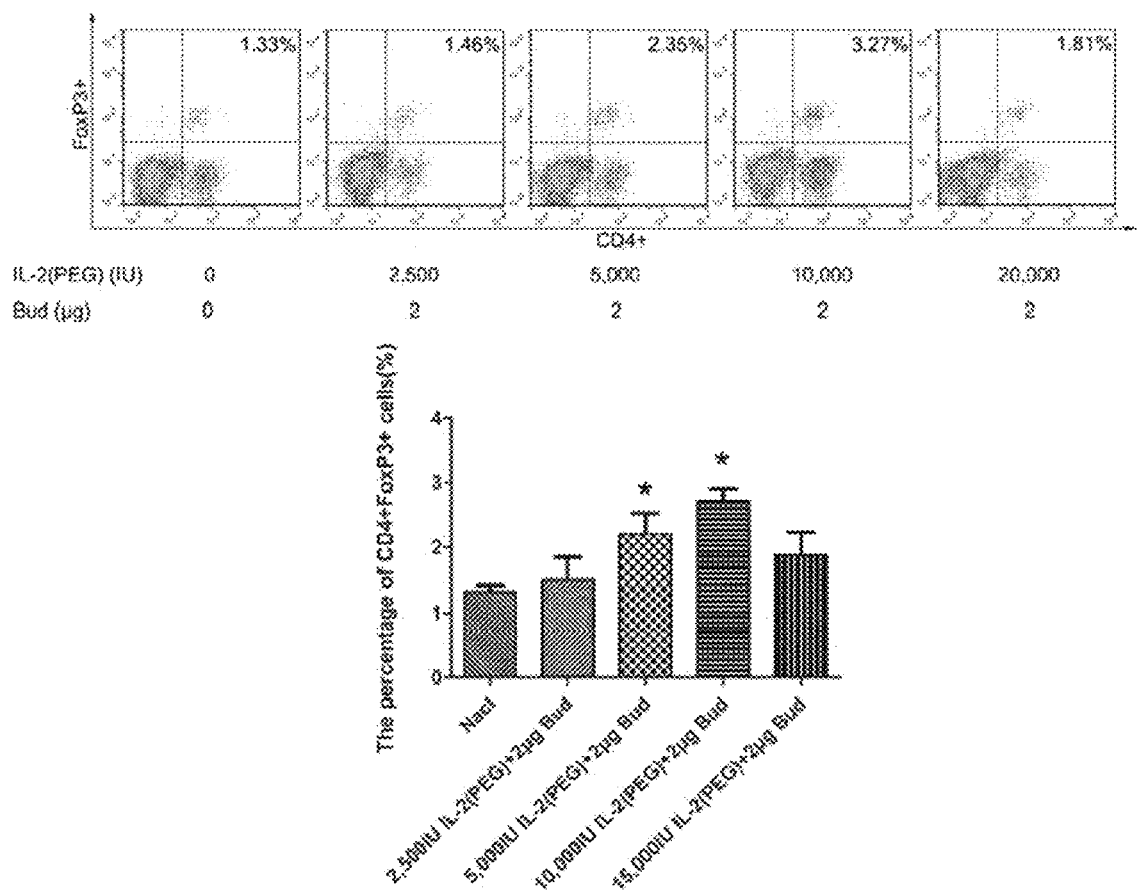
FIG. 3: Treg up-regulation level after treatment with IL-2(PEG):Bud dosage form at different medication ratios. Bud was fixed at 2 μg and combined with different doses of IL-2(PEG). Data are expressed as mean±standard deviation (n=6 per group). *group vs NaCl group P<0.05.

Modeling was carried out in the same manner as in Example 1, while administration and Treg detection were carried out in the same manner as in Example 2, and the Bud was fixed at 2 µg in combination with 2,500, 5,000, 10,000 or 20,000 IU IL-2(PEG), respectively. It was concluded that 10,000 IU IL-2(PEG) combined with 2 µg Bud (5,000 IU IL-2(PEG): 1 µg Bud) was able to maximally upregulate Treg in the airway, which was the optimal dosing ratio ($p<0.05$, FIG. 3).

Example 5

Figure 4A:
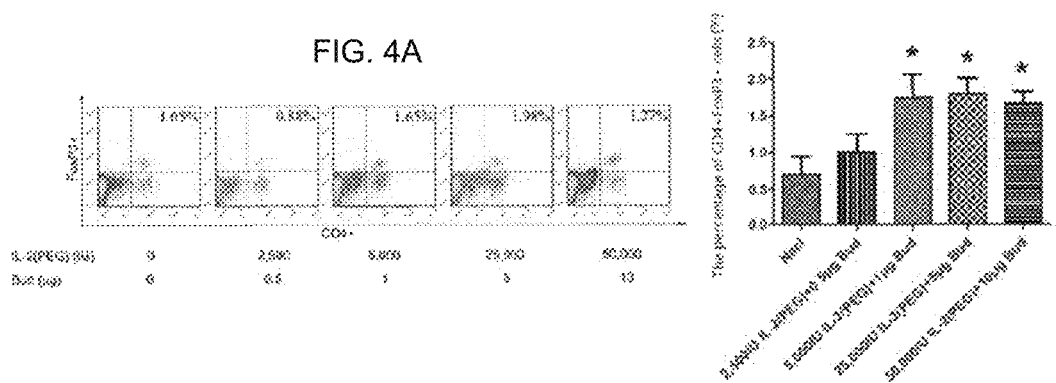
FIGS. 4A-4D: Detection of Treg upregulation level and asthma treatment indicators after treatment with IL-2(PEG): Bud dosage form at the optimal ratio and different doses.
Figure 4B:
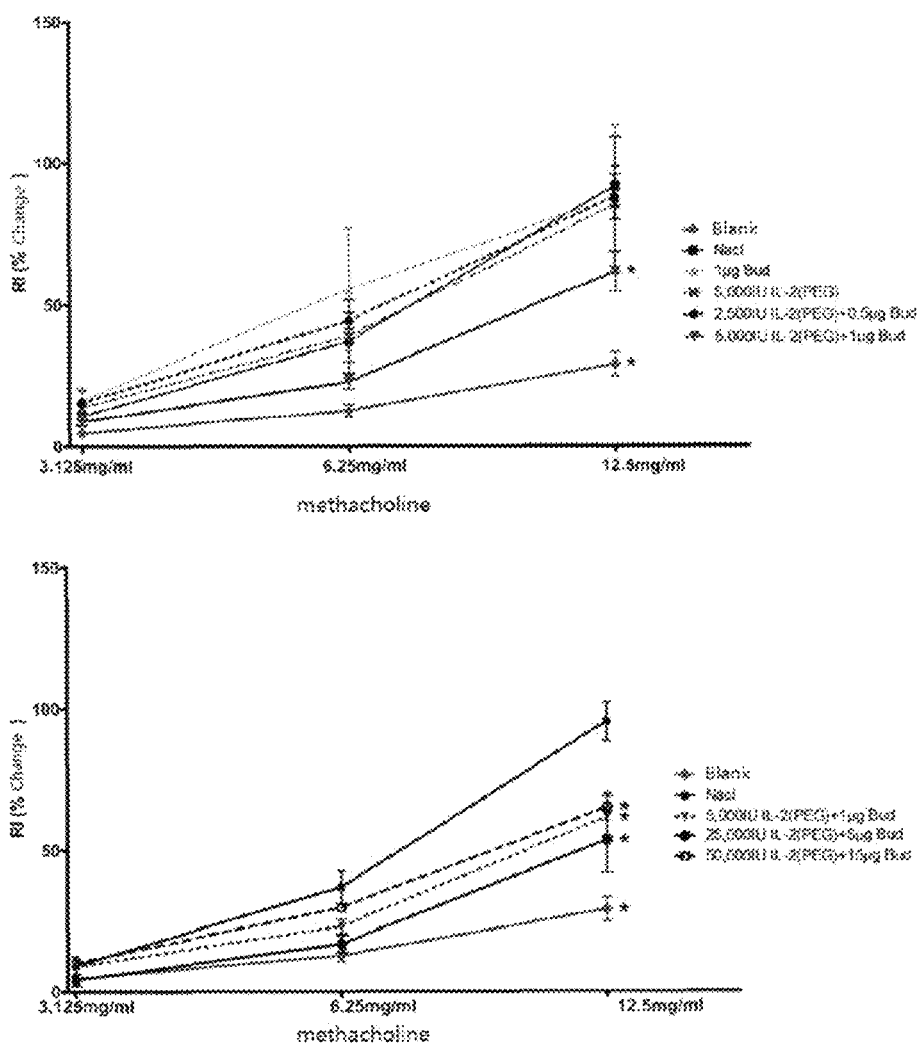
Figure 4C:
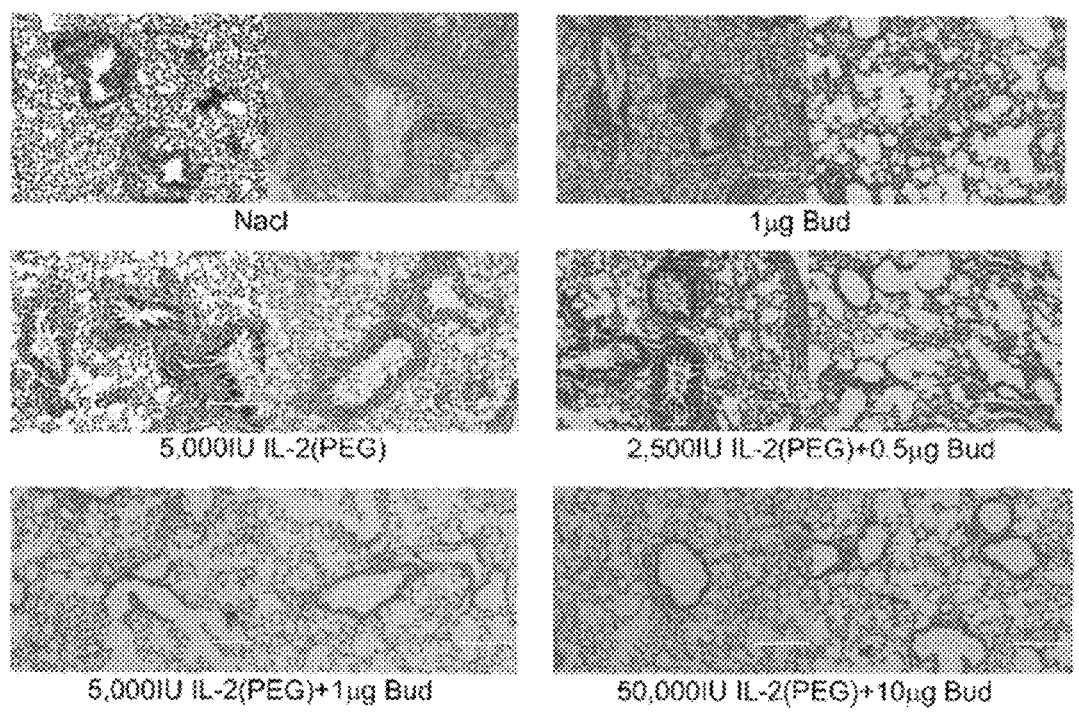

New Dosage Form of IL-2(PEG)+Bud with the Optimal Ratio had a Wide Effective Range for Upregulating Treg, and Could Exert a Therapeutic Effect at a Small Dose Modeling was carried out in the same manner as in Example 1, and administration, Treg detection and histopathological analysis were carried out in the same manner as in Example 2, and lung function measurement was carried out in the same manner as in Example 3. After 3 days of continuous administration of the high-dose (50,000 IU IL-2 (PEG): 10 µg Bud), medium-dose (25,000 IU IL-2(PEG): 5 µg Bud) and low-dose (5,000 IU IL-2(PEG): 1 µg Bud) at the optimal dose (5,000 IU IL-2(PEG): 1 µg Bud) to the asthma model mice, the cells in the bronchoalveolar lavage fluid were analyzed. It could be observed that all the three doses were effective to upregulate Treg ($p<0.05$, FIG. 4A), and when the dose was further reduced (2,500 IU IL-2 (PEG): 0.5 µg Bud), the upregulation effect disappeared. In lung function measurement and lung histopathological microscopy, it was observed that all the three doses that could upregulate Treg could improve lung pathological symptoms as well as airway compliance and airway resistance ($p<0.05$, FIGS. 4B and FIG. 4C). 2,500 IU IL-2(PEG): 0.5 µg Bud could not upregulate Treg or relieve airway resistance synchronously, further proving that Treg upregulation is associated with a therapeutic effect of relieving airway resistance.

Figure 4D:
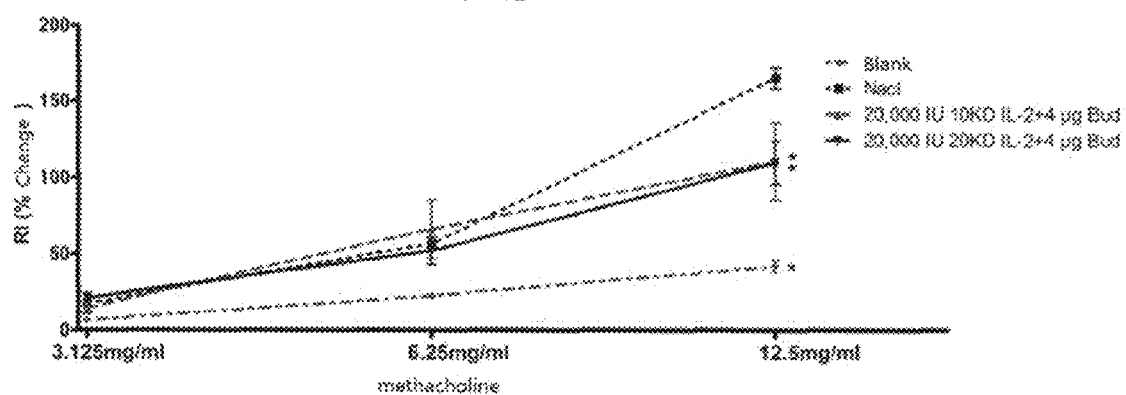

In order to determine the effect of IL-2 modified with PEG of different molecular weights in combination with a glucocorticoid, experiments were carried out using the 10 KD non-branched PEG-modified IL-2 and 20 KD branched PEG-modified IL-2 as described in Example 2, respectively. After 3 days of continuous administration of 20,000 IU PEG-modified IL-2 in combination with 4 µg Bud to the asthma mice, a decrease in airway resistance was observed, indicating a certain effect of treatment ($p<0.05$, FIG. 4D). This indicated that 10 kD, 20 kD non-branched PEG-modified IL-2 and 20 kD branched PEG-modified IL-2 had therapeutic effects on asthma.

Example 6

Local Medication of IL-2(PEG):Bud by Atomization had Rapid Onset and Remarkable Curative Effect Compared to Intraperitoneal Injection of Dex Modeling of asthma model mice and administration. The same mice as in Example 1 were used for asthma modeling, which were sensitized by intraperitoneal injection with 100 µg of ovalbumin (OVA) (Sigma) and 2 mg of $Al(OH)_3$ for injection (Sigma) on days 1 and 8, and challenged by daily nasal instillation with 20 µl of 2% OVA on days 9-18. According to the purpose of the experiment, 40 µg Dex was intraperitoneally injected on days 12-18, 14-18 and 16-18, or 25,000 IU IL-2(PEG)+5 µg Bud was administered by atomization on days 16-18, respectively.

Figure 5A:
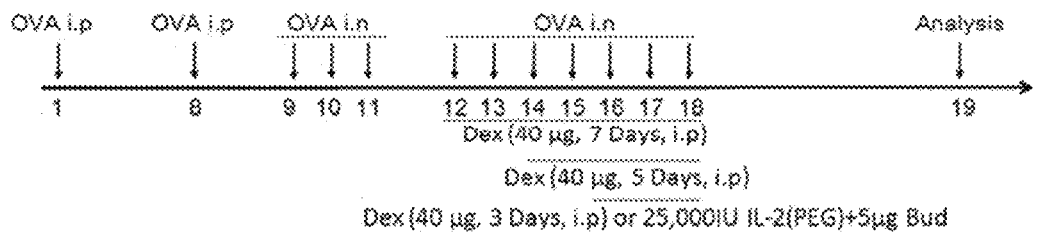
FIGS. 5A-5C: Comparison of efficacy of local atomization medication of IL-2(PEG):Bud and intraperitoneal injection of Dex.

Administration and histopathological analysis were performed in the same manner as in Example 2, and lung function test was performed in the same manner as in Example 3. It is often used clinically to treat respiratory allergic diseases including asthma by injecting Dex. Mice were continuously challenged for 10 days from the next day to the second intraperitoneal injection, and were administered on days 4, 6, and 8 after challenge (FIG. 5A). Continuous intraperitoneal injection at a dose of 40 µg Dex per mouse (equivalent to 12 mg Dex per adult of 60 kg, which is a dose for relieving asthma) for 3 or 5 days did not alleviate the airway resistance in asthma mice, and at least 7 consecutive days of intraperitoneal injection was required to exert a therapeutic effect on asthma.

Figure 5B:
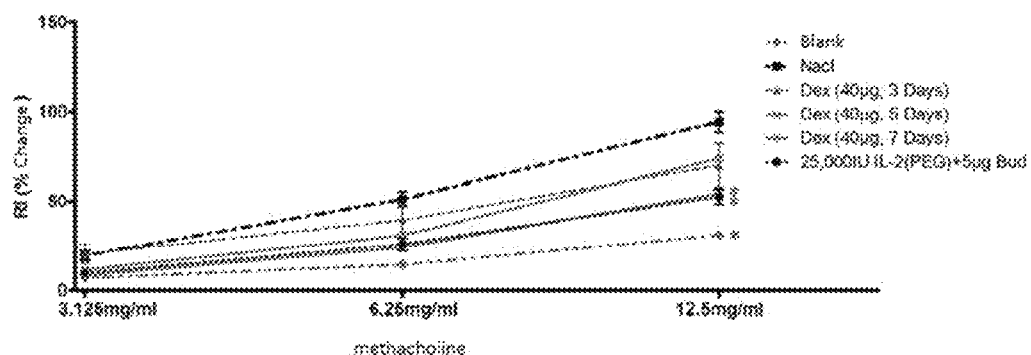
Figure 5C:
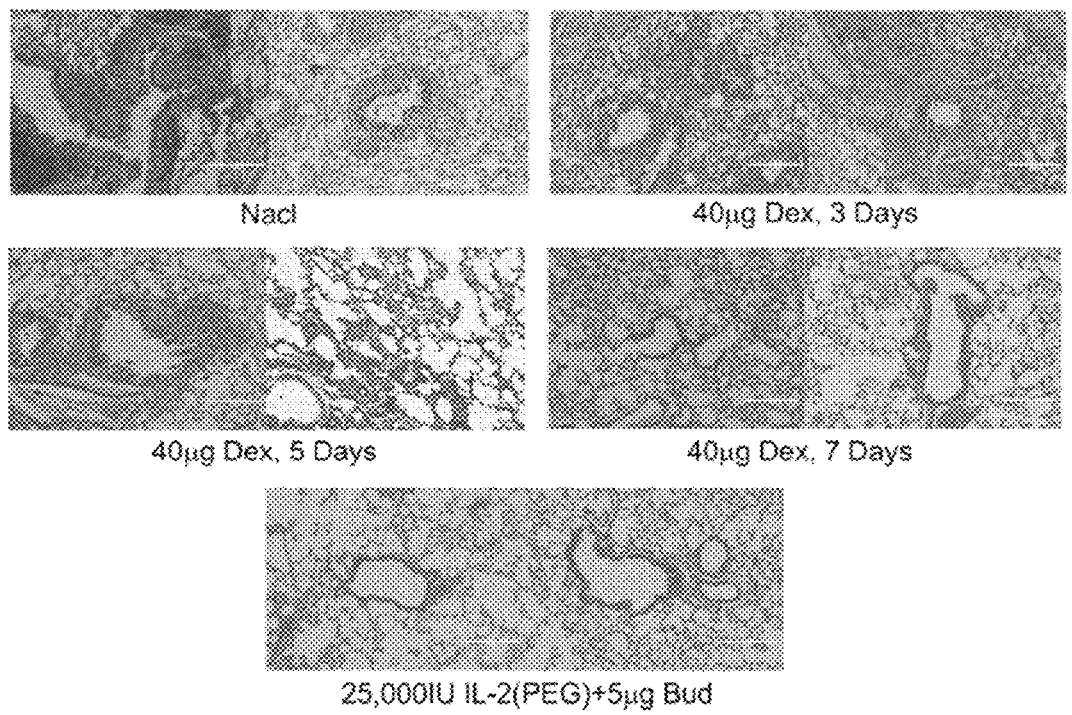

However, local atomization treatment for the respiratory tract with a small dose (25,000 IU IL-2(PEG)+5 µg Bud) (administered in the same way as in FIG. 5A) could achieve the same level of therapeutic effect after only three days of treatment (FIGS. 5B and 5C).

Example 7

Figure 6A:
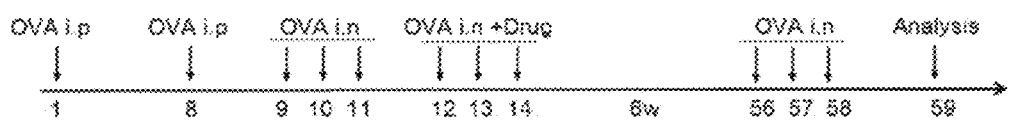
FIGS. 6A-6C: Evaluation of treatment effect after 6 weeks of local medication of IL-2(PEG):Bud.
Figure 6B:
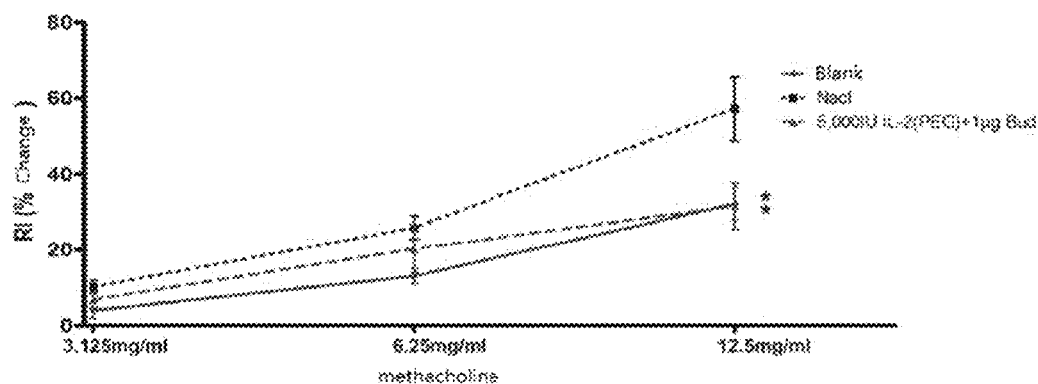
Figure 6C:
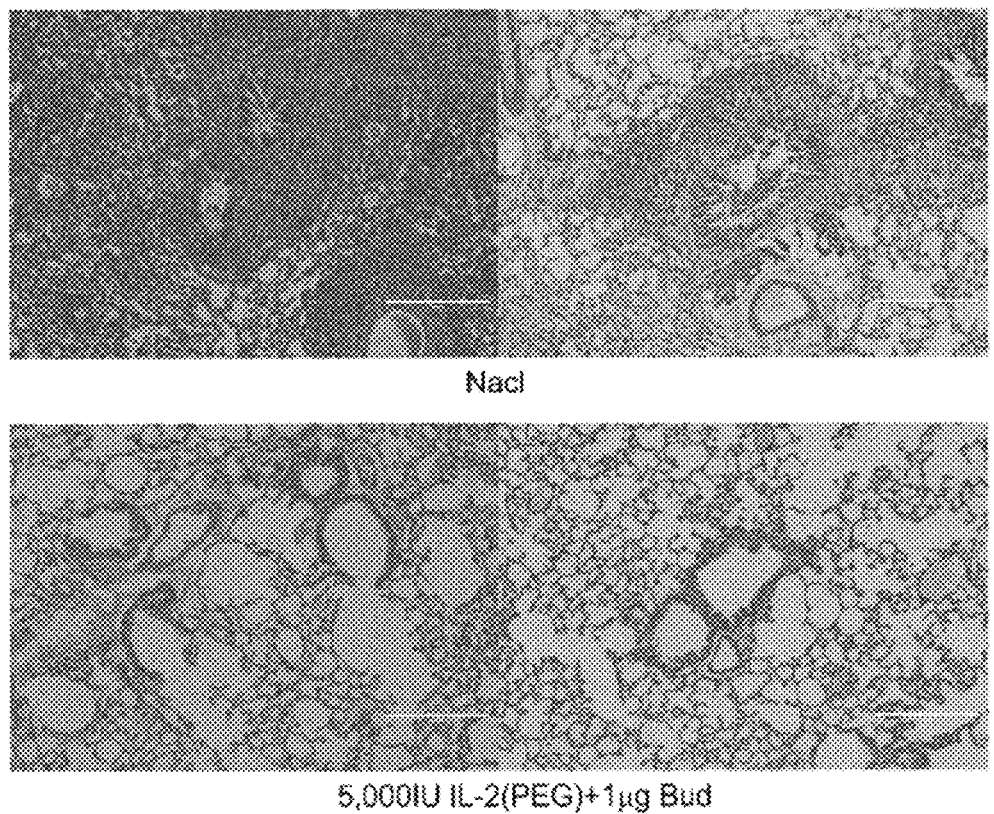

Local Combination Medication for the Respiratory Tract could Maintain a Therapeutic Effect for at Least 6 Weeks Modeling of asthma model mice and administration. The same mice as in Example 1 were used for asthma modeling, which were sensitized by intraperitoneal injection with 100 µg of ovalbumin (OVA) (Sigma) and 2 mg of Al(OH)3 for injection (Sigma) on days 1 and 8, and challenged by daily nasal instillation with 20 µl of 2% OVA on days 9-11 and 12-14. Drug intervention was performed on days 12 to 14 after modeling, and after 6 weeks, 20 µl of 2% OVA was used again for challenge for three consecutive days on days 56-58. The combined treatment (the combined drugs and the ratios and the doses were the same as in Example 6) was performed through local atomization administration in the respiratory tract for three days (FIG. 6A). In the lung function measurement of the mice, it could be observed that compared with the mice treated with only saline (the group showed poor airway compliance), although the mice in the combination medication group were poorer in lung function than the healthy mice after challenge with a lower concentration of methacholine, they had a lung function that was essentially equal to that of healthy mice after challenge with 12.5 mg/ml of methacholine. The pathological manifestations of lung tissue also indicated that the effects of drug treatment were maintained for at least 6 weeks (FIGS. 6B and 6C). And the long-term effect was similar to the short-term effect.

Example 8

Figure 7A:
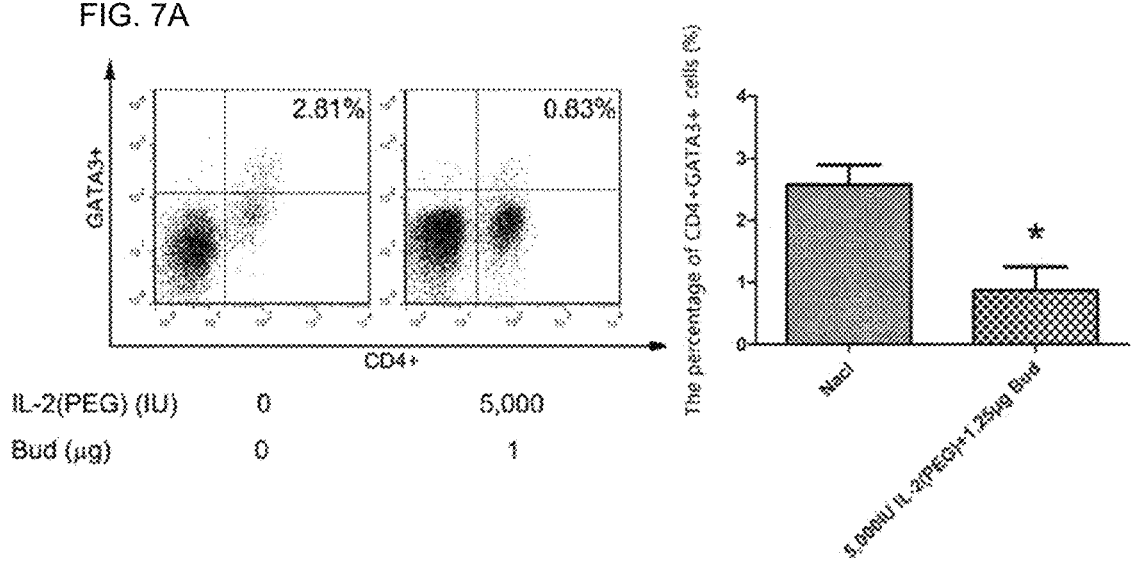
FIGS. 7A-7B: Measurement of Th2 cells and cytokines in bronchoalveolar lavage fluid after local application of IL-2 (PEG):Bud.
Figure 7B:
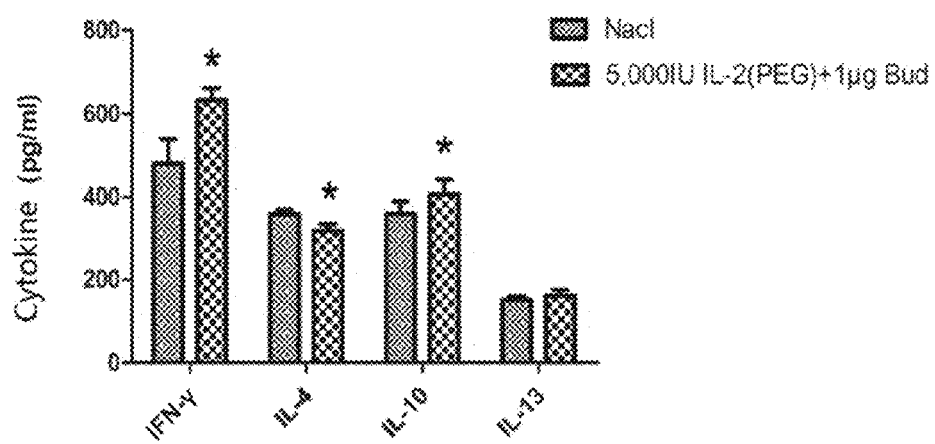

The Action Mechanism of Combination Medication is to Relatively Downregulate Th2 Cells, and the Upregulated Treg can Exert Immune-Regulatory Effects by Secreting Anti-Inflammatory Factors Molding was carried out in the same manner as in Example 1, and administration (the combined drugs and the ratios and the doses were the same as in Example 6), Th2 detection, and cytokine detection were carried out in the same manner as in Example 2. As a key effector T cell that promotes the onset of asthma, the Th2 cells (CD4+gata3+) in the cells of bronchoalveolar lavage fluid of the mice after combination medication were also analyzed. It was found that after combination medication, the ratio of Th2 was significantly downregulated while the Treg cells were increased (FIG. 7A), demonstrating that combination medication increased Treg while regulating the ratio of Th2/Treg, which is a key factor leading to the onset of asthma, and asthma was treated from the pathogenesis[1, 7]. Analysis of cytokines in bronchoalveolar lavage fluid revealed that the pathogenic cytokine IL-4, which induces the secretion of IgE antibodies from B cells, was downregulated after combination medication, while the cytokines IFN-γ and IL-10, which regulate immune balance, increased after medication. In addition, IL-13, which promotes mucus secretion, showed no significant difference between the two groups, suggesting that it is not the key to the mechanism of asthma treatment of combination medication (FIG. 7B).

Example 9

In Vitro Treg Inhibition Experiments Showed that the Treg Induced by Combination Medication was Non-Specific Treg Collection of spleen lymphocytes. Mouse spleen tissues were harvested under aseptic conditions, and grounded in PBS. Single cells were collected by a single cell strainer (BD), centrifuged to remove PBS, subjected to red blood cell lysis treatment with a red blood cell lysis buffer (TIAN-GEN), washed again with PBS, and resuspended in 1640 medium (Gibco) to obtain a spleen cell suspension.

In vitro Treg inhibition experiment. Molding was carried out in the same manner as in Example 1 and administration (the combined drugs and the ratios and the doses were the same as in Example 6) was carried out in the same manner as in Example 2. Lymphocytes in the spleen of DO10.11 mice (OVA-specific TCR transgenic mice) were isolated using a CD4+CD25+ flow sorting kit. Bronchoalveolar lavage fluid of the asthma mice after medication was aseptically collected. The Treg was obtained using a flow sorting method. About $10^5$ cells per mouse were obtained. To the culture system of the isolated spleen lymphocytes of DO10.11 mice, OVA was added, in addition, the spleen cells of healthy BALB/c mice and Treg sorted from the bronchoalveolar lavage fluid of the asthma mice after drug treatment were added, respectively, and cultured in 1640 medium containing 10% serum for 24 hours, and subjected to CFSE staining to measure cell proliferation.

The results showed that the addition of OVA to the culture system of spleen lymphocytes of DO10.11 mice could significantly promote the proliferation of effector T cells. Both the addition of nTreg sorted from the spleen cells of unsensitized mice, and the addition of the Treg produced in asthma model mice after combination medication could effectively inhibit the proliferation of T cells triggered by this specific antigen (FIG. 8A).

A lymphocyte reaction system was constructed on a 96-well plate, with about $10^5$ female BALB/c mouse spleen cells in each well, in which about $10^5$ C57BL/6 mice spleen cells treated with mitomycin were added to stimulate proliferation, forming a mixed lymphocyte reaction system. The spleen cells of healthy BALB/c mice and Treg sorted in bronchoalveolar lavage fluid of asthma mice after drug treatment were added, respectively, and cultured in 1640 medium containing 10% serum for 24 hours, and subjected to CFSE staining to measure cell proliferation.

Figure 8:
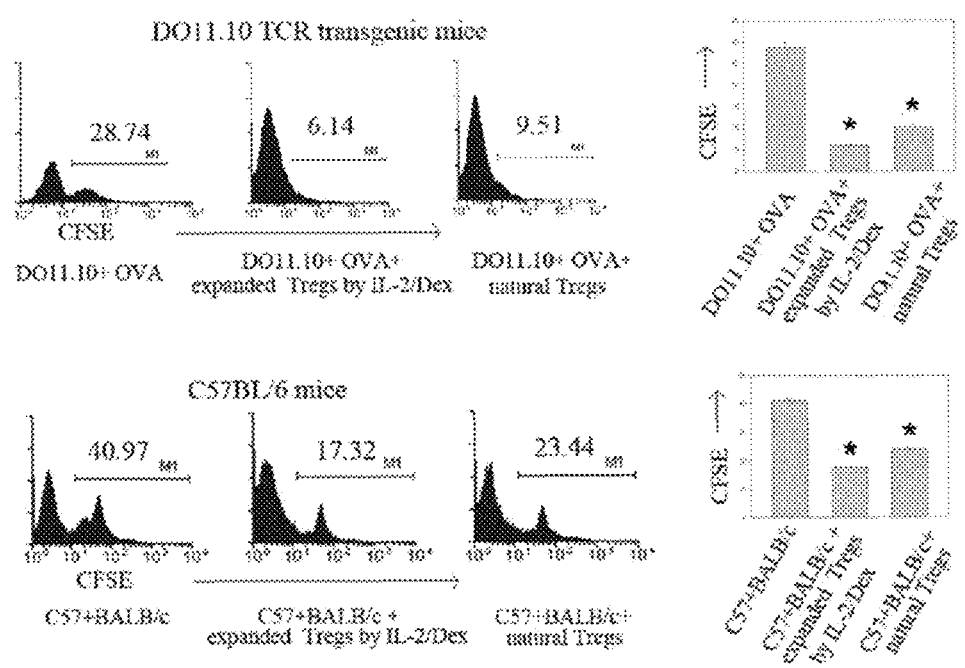
FIGS. 8A-8B: Specific and non-specific inhibitory effects of iTreg in bronchoalveolar lavage fluid obtained by flow sorting after drug induction.

The results showed that both the addition of nTreg sorted from the spleen cells of unsensitized mice, and the addition of the Treg produced in asthma model mice after combination medication had similar effects of inhibiting lymphocyte activation and proliferation (FIG. 8B).

Example 10

Local Medication had No Systemic Effect

Figure 9A:
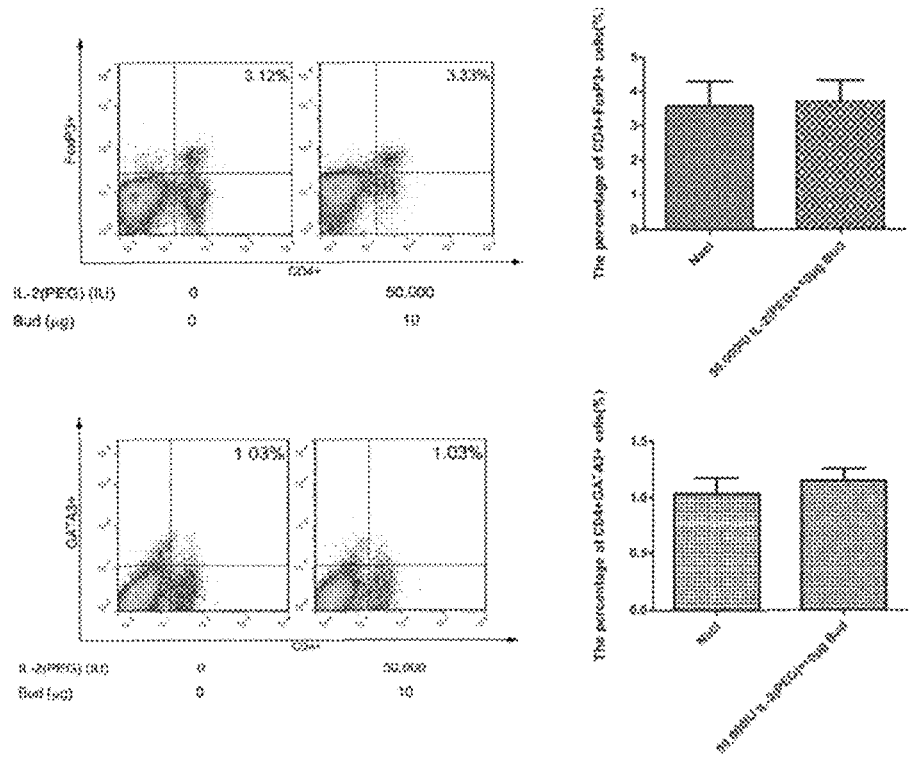
FIGS. 9A-9B: After treatment with local medication.
Figure 9B:
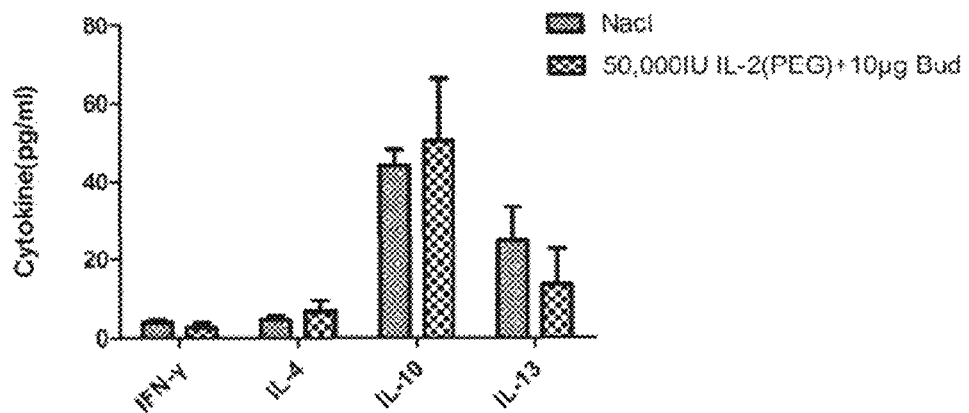

In our previous studies, systemic medication was able to upregulate Treg in spleen cells, which may have an effect on autoimmune homeostasis[13]. Modeling was carried out in the same manner as in Example 1 and administration (the combined drugs and the ratios and the doses were the same as in Example 6) was carried out in the same manner as in Example 2, and the spleen cells were collected. The ratio of Treg to Th2 in spleen cells of asthma model mice with and without medication was analyzed, and no significant difference was found ($P>0.05$, FIG. 9A). In addition, there were no significant differences in several cytokines, which were different in bronchoalveolar lavage fluid, in the serum of the mice in the two groups ($p>0.05$, FIG. 9B).

REFERENCES

1. Holgate S T. The epidemic of asthma and allergy. J R Soc Med 2004; 97(3):103-10.
2. Gupta R, Anderson H R, Strachan D P, Maier W, Watson L. International trends in admissions and drug sales for asthma. Int J Tuberc Lung Dis 2006; 10(2):138-45.
3. Robinson D S. The role of the T cell in asthma. J Allergy Clin Immunol 2010; 126(6):1081-91; quiz 1092-3.
4. Vignali D A, Collison L W, Workman a How regulatory T cells work. Nat Rev Immunol 2008; 8(7):523-32.
5. Fehervari Z, Sakaguchi S. Development and function of CD25+CD4+ regulatory T cells. Curr Opin Immunol 2004; 16(2):203-8.
6. Robinson D S. Regulatory T cells and asthma. Clin Exp Allergy 2009; 39(9):1314-23.
7. Shi Y H, Shi G C, Wan H Y, Ai X Y, Zhu H X, Tang W, et al., An increased ratio of Th2/Treg cells in patients with moderate to severe asthma. Chin Med J (Engl) 2013; 126(12):2248-53.
8. Stelmaszczyk-Emmel A, Zawadzka-Krajewska A, Szypowska A, Kulus M, Demkow U. Frequency and activation of CD4+CD25 FoxP3+ regulatory T cells in peripheral blood from children with atopic allergy. Int Arch Allergy Immunol 2013; 162(1):16-24.
9. Jeffery L E, Burke F, Mura M, Zheng Y, Qureshi O S, Hewison M, et al. 1,25-Dihydroxyvitamin D3 and IL-2 combine to inhibit T cell production of inflammatory cytokines and promote development of regulatory T cells expressing CTLA-4 and FoxP3. J Immunol 2009; 183(9): 5458-67.

10. Wilson M S, Pesce J T, Ramalingam T R, Thompson R W, Cheever A, Wynn T A. Suppression of murine allergic airway disease by IL-2:anti-IL-2 monoclonal antibody-induced regulatory T cells. J Immunol 2008; 181(10):6942-54.

11. Chen X, Oppenheim J J, Winkler-Pickett R T, Ortaldo J R, Howard O M. Glucocorticoid amplifies IL-2-dependent expansion of functional FoxP3(+)CD4(+)CD25(+) T regulatory cells in vivo and enhances their capacity to suppress EAE. Eur J Immunol 2006; 36(8):2139-49.

12. Kearley, J., J. E. Barker, D. S. Robinson, and C. M. Lloyd. 2005. Resolution of airway inflammation and hyperreactivity after in vivo transfer of CD4+CD25+ regulatory T cells is interleukin 10 dependent. J Exp Med. 202:1539-47.

13. Ma J, Yang A, Qin W, Shi Y, Zhao B, Jin Y, et al., Alleviating allergic airway diseases by means of short-term administration of IL-2 and dexamethasone. J Allergy Clin Immunol 2011; 127(6):1447-56.e6.

14. Thornton E E, Looney M R, Bose O, Sen D, Sheppard D, Locksley R, et al., Spatiotemporally separated antigen uptake by alveolar dendritic cells and airway presentation to T cells in the lung. J Exp Med 2012; 209(6):1183-99.

15. Fontenot J D, Gavin M A, Rudensky A Y. Foxp3 programs the development and function of CD4+CD25+ regulatory T cells. Nat Immunol 2003; 4(4):330-6.

16. Fishburn C S. The pharmacology of PEGylation: balancing PD with PK to generate novel therapeutics. J Pharm Sci 2008; 97(10):4167-83.

17. Cetinkaya F, Tufekci B S, Kutluk G. A comparison of nebulized budesonide, and intramuscular, and oral dexamethasone for treatment of croup. Int J Pediatr Otorhinolaryngol 2004; 68(4):453-6.

The invention claimed is:

1. An inhalable pharmaceutical composition, comprising a polyethylene glycol (PEG)-modified interleukin 2 (IL-2) and a glucocorticoid, and optionally a pharmaceutically acceptable carrier and/or excipient, wherein the IL-2 is a human IL-2 and wherein the PEG modification is at a N-terminal amino acid residue of IL-2.

2. The pharmaceutical composition of claim 1, wherein the glucocorticoid is one or more selected from the group consisting of dexamethasone (Dex), budesonide (Bud), beclomethasone dipropionate (BDP), ciclesonide, hydrocortisone, cortisone, prednison, prednisolone, methylprednisolone, triamcinolone, betamethasone, clobetasone butyrate, triamcinolone acetonide, fluocinolone acetonide, mometasone furoate, halcinonide, clobetasol propionate, halcinonide, halometasone monohydrate and diflorasone diacetate.

3. The pharmaceutical composition of claim 1, wherein the PEG modification is a modification of IL-2 with a non-branched PEG or a branched PEG.

4. The pharmaceutical composition of claim 1, formulated:

(1) in a form of dry powder composition, optionally comprising one or more suitable diluents or carriers; or (2) in a form of pressurized metered dose inhalation, wherein both the PEG-modified IL-2 and the glucocorticoid are suspended or completely dissolved in a liquid propellant mixture.

5. The pharmaceutical composition of claim 1, wherein the ratio of the PEG-modified IL-2 to the glucocorticoid is between 1,000 IU IL-2(PEG):1 μg glucocorticoid and 10,000 IU IL-2(PEG):1 μg glucocorticoid.

SEQUENCE LISTING

```
<160> NUMBER OF SEQ ID NOS: 1

<210> SEQ ID NO 1
<211> LENGTH: 133
<212> TYPE: PRT
<213> ORGANISM: Homo sapiens

<400> SEQUENCE: 1

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
    130
```

6. The pharmaceutical composition of claim 1, wherein the PEG-modified IL-2 is present in the composition at a dose between 3,000 IU and 100,000 IU.

7. The pharmaceutical composition of claim 1, wherein the PEG modification is a modification of IL-2 with a non-branched PEG or a branched PEG with a molecular weight of 2-60 KD.

8. The pharmaceutical composition of claim 1, wherein the IL-2 is modified at its N-terminus with the PEG.

9. The pharmaceutical composition of claim 1, wherein the glucocorticoid is Dex, and the ratio of the PEG-modified IL-2 to the Dex is 4,000 IU IL-2(PEG):1 μg Dex.

10. The pharmaceutical composition of claim 9, wherein the PEG-modified IL-2 is present in the composition at a dose between 7,500 IU and 80,000 IU.

11. The pharmaceutical composition of claim 1, wherein the glucocorticoid is Bud, and the ratio of the PEG-modified IL-2 to the Bud is 5,000 IU IL-2(PEG):1 μg Bud.

12. The pharmaceutical composition of claim 11, wherein the PEG-modified IL-2 is present in the composition at a dose between 3,500 IU and 80,000 IU.

13. The pharmaceutical composition of claim 1, wherein the glucocorticoid is BDP and the ratio of the PEG-modified IL-2 to the BDP is 5,000 IU IL-2(PEG):1 μg BDP.

14. The pharmaceutical composition of claim 13, wherein the PEG-modified IL-2 is present in the composition at a dose between 3,500 IU and 80,000 IU.

15. The pharmaceutical composition of claim 1, wherein the IL-2 is set forth in SEQ ID NO. 1.

16. The pharmaceutical composition of claim 1, wherein the N-terminal amino acid residue comprises lysine, serine or threonine.

17. The pharmaceutical composition of claim 1, wherein the PEG modification is at the N-terminal alpha-amino of IL-2.

* * * * *